(12) United States Patent
Greenfield et al.

(10) Patent No.: US 7,270,976 B2
(45) Date of Patent: Sep. 18, 2007

(54) METHODS FOR MEASURING ADAMTS13 ACTIVITY AND PROTEIN ON PLATELETS AND IN PLASMA

(75) Inventors: Robert S. Greenfield, Trumbull, CT (US); Safi Ranzurmal, Milford, CT (US)

(73) Assignee: American Diagnostica, Inc., Stamford, CT (US)

( * ) Notice: Subject to any disclaimer, the term of this patent is extended or adjusted under 35 U.S.C. 154(b) by 204 days.

(21) Appl. No.: 10/894,702

(22) Filed: Jul. 19, 2004

(65) Prior Publication Data

US 2006/0014233 A1    Jan. 19, 2006

(51) Int. Cl.
   *C12Q 1/37* (2006.01)
(52) U.S. Cl. ...................................................... 435/23
(58) Field of Classification Search ............... None
   See application file for complete search history.

(56) References Cited

U.S. PATENT DOCUMENTS

| | | |
|---|---|---|
| 2002/0136713 A1 | 9/2002 | Laemmle et al. |
| 2003/0073136 A1 | 4/2003 | Ginsburg et al. |
| 2003/0083231 A1 | 5/2003 | Ahlem et al. |
| 2004/0138187 A1 | 7/2004 | Reading et al. |

FOREIGN PATENT DOCUMENTS

WO    WO 2004-035778    4/2004

OTHER PUBLICATIONS

Kasili et al. J. Am. Chem. Soc. 2004;126:2799-2806.*
Zablotna et al. Biochem and Biophy Res Commu 2004;(319):185-188.*
Pattanaik et al. Biochem and Biophy Res Commu 2003;(309):974-979.*
Richard Lottenberg, et al., *Assay Of Coagulation Proteases Using Peptide Chromogenic And Fluorogenic Substrates*, Methods In Enzymology. vol. 80, p. 341-361.
International Search Report for PCT/US04/23177 dated Jun. 23, 2005.
Furlan et al, *Deficient Activity of von Willebrand Factor-Cleaving Protease in Chronic Relapsing Thrombotic Thrombocytopenic Pupura*; Blood, vol. 89; No. 9; 1997; pp. 3097-3103.
Furlan et al., *Assays if von Willebrand Factor-Cleaving Protease: A Test for Diagnosis of Familial and Acquired Thrombotic Thrombocytopenic Purpura*; Seminars in Thrombosis and Hemostasis; vol. 28; No. 2; 2002; pp. 167-172.
Gerritsen et al., *Assay of von Willebrand Factor(vWF)-cleaving Protease Based on Decreased Collagen Binding Affinity of Degraded vWF*; Thromb Haemost; vol. 82; 1999; pp. 1386-1389.
Klaus, et al., *Epitope mapping of ADAMTS13 autoantibodies in acquired thrombotic thrombocytopenic purpura*; Blood; vol. 103; No. 12; 2004; pp. 4514-4519.
Laffan et al., *The diagnosis of von Willebrand disease: a guideline from the UK Haemophilia Centre Doctors' Organization*; Haemophilia; vol. 10; 2004; pp. 199-217.
Joel L. Moake, *Thromboic Thrombocytopenic Purpura and the Hemolytic Uremic Syndrome*; Arch Pathol Lab Med.; vol. 126; 2002; pp. 1430-1433.
Obert et al., *Estimaton of the von Willebrand Factor-cleaving Protease in Plasma Using Monoclonal Antibodies to vWf*; Thromb Haemost; vol. 82; 1999; pp. 1382-1385.
J. Evan Sadler, *A new name in thrombosis, ADAMTS13*; PNAS; vol. 99; No. 18; 2002; pp. 11552-11554.
Zhou, et al., *An enzyme immunoassay of ADAMTS13 distinguishes patients with thrombiotic thrombocytopenic purpura from normal individuals and carriers of ADAMTS13 mutations*; Thromb Haemost; vol. 91; 2004; pp. 806-811.
Suzuki et al., *Detection of von Willebrand factor-cleaving protease(ADAMTS-13) in human platelets*; Biochemical and Biophysical Research Communications; vol. 313; 2004; pp. 212-216.
Tsai et al., *von Willebrand Factor and von Willebrand Factor-Cleaving Metalloprotease Activity in Escherichia coli O157:H7-Associated Hemolytic Uremic Syndrome*; Pediatric Research; vol. 49; No. 5; 2001; pp. 653-659.
Tsai et al., *von Willebrand factor, ADAMTS13, and thrombotic thrombocytopenic purpura*; J Mol Med; vol. 80; 2002; pp. 639-647.
Yarranton et al.; *Thrombotic Thrombocytopenic Purpura: New Approaches to Diagnosis and Management*; Blood Therapies in Medicine; vol. 2; No. 3; 2002; pp. 82-91.
Zheng et al., *Structure of von Willebrand Factor-cleaving Protease(ADAMTS13), a Metalloprotease Involved in Thrombotic Thrombocytopenic Purpura*; The Journal of Biological Chemistry; vol. 276; No. 44; 2001; pp. 41059-41063.

* cited by examiner

*Primary Examiner*—Ralph Gitomer
*Assistant Examiner*—Bin Shen
(74) *Attorney, Agent, or Firm*—Frommer Lawrence & Haug LLP; Sandra Kuzmich; Anne-Marie C. Yvon

(57) ABSTRACT

Provided are assays to detect ADAMTS13 activity using peptide substrates. These assays can be used for diagnostic applications and to evaluate treatment of thrombotic thrombocytopenic purpura (TTP). Also provided is a novel form of ADAMTS13 found on platelets.

64 Claims, 20 Drawing Sheets

A

B

METHODS FOR MEASURING ADAMTS13 ACTIVITY AND PROTEIN ON PLATELETS AND IN PLASMA

FIELD OF THE INVENTION

The invention provides assays for measurement of ADAMTS13 activity and diagnosis of thrombotic thrombocytopenia purpura.

BACKGROUND OF THE INVENTION

Thrombotic Thrombocytopenia Purpura (TTP) is a life threatening thrombotic microangiopathic disease characterized by hemolytic anemia and thrombocytopenia associated with platelet aggregation. The cause of TTP has been recently linked to abnormalities in a metalloproteinase called ADAMTS13 or von Willebrand factor cleaving protease. ADAMTS13 is an enzyme that is present in significant levels in plasma, and may be expressed in other tissues (Levy et al. 2001, Nature 413:488-494; Plaimauer et al. 2002, Blood 100:3626-3632). Suzuki et al. (2004, Biochem. Biophys. Res. Com. 313:212-216) recently reported ADAMTS13 in platelets.

ADAMTS13 functions by cleaving ultralarge von Willebrand factor (VWF) multimers to smaller VWF proteins. Decreased VWF cleaving protease activity leads to persistence of unusually large multimers of VWF that bind to platelets, causing platelet aggregates, microangiopathic hemolysis, and thrombocytopenia in patients with TTP. Clinical manifestations of TTP are difficult to distinguish from hemolytic uremic syndrome (HUS), another thrombotic microangiopathic disorder. Recent studies indicate that low levels of ADAMTS13 activity are associated with TTP, but not HUS (Veyradier A, et al. 2002, Blood 98:1765-1772; Furlan et al. 1998, Blood 91:2839-2846). Thus, differential diagnosis of TTP can be made by measuring ADAMTS13 activity.

There are two forms of TTP—congenital (familial) and acquired (Furlan et al. 1996, Blood 87:4223-4234; Furlan et al. 1998, Blood 91:2839-2846). Congenital TTP is caused by genetic mutations in the ADAMTS13 gene, which result in a loss in ADAMTS13 production and/or the production of a non-functional ADAMTS13 enzyme. Acquired TTP is an autoimmune-like disease, which has been linked to intake of certain pharmaceutical drugs. Acquired TTP is caused by the generation of autoantibodies to ADAMTS13 protein. The onset of acquired TTP has been linked to intake of certain pharmaceutical drugs.

Several methods for measuring the presence and/or activity of ADAMTS13 are known in the art. These methods include collagen binding assays, ristocetin cofactor assays, electrophoretic analysis (e.g. multimer analysis) and immunological methods. Electrophoretic immunoassays, such as Western blotting analysis, have largely been replaced by immunoradiometric assays (IRMA) and enzyme-linked immunosorbant assays (ELISA) (Laffan et al. 2004, Haemophilia 10:199-217). Several reports describe ADAMTS13 assays where the A2 domain of VWF is used as a substrate (Zhou et al. 2004, Thromb. Haemost. 91:806-811; Kokame et al. 2004, Hemost. Thromb. Vasc. Biol. Blood 103:607-612; Cruz et al. 2004, Thromb. Haemost. 90:1204-1209). Cleavage of the A2 domain is monitored by an ELISA method. The available assays for ADAMTS13 require a relatively high technical skill level, and are therefore not performed in most clinical laboratories. In addition, obtaining results can take several days using available tests, which is detrimental to patients presenting with TTP, who require rapid diagnosis.

A simple, specific and rapid assay for ADMTS13 is needed to solve the problems with the currently available assays; yet one has not been developed to date. Attempts at developing such an assay using ADAMTS13 isolated from plasma have not been successful. Furlan et al. tested 28 synthetic chromogenic peptidyl substrates with para-nitroanaline (pNA) as the leaving group, and did not observe consistent, repeatable results (2002 Seminars in Thrombosis and Hemostasis 28(2):167-172). These results demonstrate the difficulty in the art of developing a rapid, reliable assay for ADAMTS13 activity.

We have discovered that ADAMTS13 on platelets has an enhanced ability, relative to ADAMTS13 in plasma, to cleave small peptidyl substrates. The difference between plasma and platelet ADAMTS13 is likely due to the finding that platelet ADAMTS13 is cleaved, while plasma ADAMTS13 is not cleaved and remains a single polypeptide. The ADAMTS13 activity on platelets can be enhanced by treatment with coagulation Factor XIa (FXIa). This indicates that activated FXI (FXIa) may cause cleavage of ADAMTS13. We have developed diagnostic chromogenic assays for measuring ADAMTS13 activity on platelets and in plasma using different peptidyl substrates with leaving groups other than pNA. We have also developed an assay method to measure autoantibodies to ADAMTS13 and an ELISA for measuring ADAMTS13 protein in plasma.

SUMMARY OF THE INVENTION

In one aspect, the invention provides a method for measuring ADAMTS13 activity comprising (a) incubating a sample comprising ADAMTS13 with a substrate, wherein the substrate comprises a peptide moiety and a chromogenic or fluorogenic moiety, wherein the peptide moiety comprises X-Val-Tyr, X-Leu-Tyr or X-Ile-Tyr, wherein X is any amino acid, and wherein the chromogenic moiety is not para-nitroanaline (pNA); and (b) measuring optical density or fluorescence of the sample; thereby measuring ADAMTS13 activity.

In a second aspect the invention provides a method for measuring ADAMTS13 activity comprising (a) incubating a sample comprising ADAMTS13 with a substrate, wherein the substrate comprises X-peptide moiety-Z, wherein the peptide moiety comprises Val-Tyr-Met, Leu-Tyr-Met or Ile-Tyr-Met, wherein X is a donor moiety and Z is an acceptor moiety, and wherein the donor and acceptor moieties mediate fluorescence resonance energy transfer; and (b) measuring fluorescence of the sample; thereby measuring ADAMTS13 activity.

Also provided by the invention is an ADAMTS13 protein isolated from platelets, wherein the ADAMTS13 protein is cleaved into more than one peptide, and wherein at least one cleaved peptide has a molecular weight on an SDS-PAGE gel of about 120 kD or less than 120 kD.

The invention also provides a method for making an ADAMTS13 substrate for measuring ADAMTS13 activity comprising covalently linking a peptide moiety to a chromogenic or fluorogenic moiety, wherein the peptide moiety comprises X-Val-Tyr, X-Leu-Tyr or X-Ile-Tyr, wherein X is any amino acid, and wherein the chromogenic moiety is not pNA.

In a fifth aspect, the invention provides a method for making an ADAMTS13 substrate for measuring ADAMTS13 activity comprising covalently linking a donor moiety, a peptide moiety and an acceptor moiety sequentially, wherein the peptide moiety comprises Val-Tyr-Met, Leu-Tyr-Met or Ile-Tyr-Met, and wherein the donor and acceptor moieties mediate fluorescence resonance energy transfer.

In another aspect, the invention provides a method for inhibiting ADAMTS13 activity comprising incubating a sample comprising ADAMTS13 with an inhibitory antibody against ADAMTS13.

In a further aspect, the invention provides a method for identifying an inhibitor of ADAMTS13 comprising (a) incubating a sample comprising ADAMTS13 with a candidate inhibitor of ADAMTS13; and measuring ADAMTS13 activity in the test sample according to the method of the first or second aspect of the invention; wherein the inhibitor is identified by reduced ADAMTS13 activity in the sample compared with ADAMTS13 activity in a control sample comprising ADAMTS13, wherein the control sample was not incubated with the candidate inhibitor.

The invention additionally provides a method for measuring the amount of ADAMTS13 in a sample comprising (a) binding anti-ADAMTS13 antibody to a solid phase; (b) adding the sample to the solid phase, wherein ADAMTS13 present in the sample binds to the antibody; (c) detecting bound ADAMTS13 using direct or indirect immunolabelling; and (d) quantifying ADAMTS13 detected; thereby measuring the amount of ADAMTS13 in the sample.

Another method provided by the invention is a method for detecting anti-ADAMTS13 antibodies in a test sample comprising (a) binding an anti-ADAMTS13 antibody raised in a first species to a solid phase; (b) adding ADAMTS13 to the solid phase, wherein the ADAMTS13 binds to the antibody raised in the first species; (c) adding the test sample to the solid phase, wherein the sample is from a second species and wherein anti-ADAMTS13 antibodies present in the test sample bind to the ADAMTS13; (d) adding a labelled antibody against antibodies from the second species, wherein the labeled antibody is raised in a third species, wherein the labeled antibody binds to the anti-ADAMTS13 antibodies bound to the ADAMTS13; and (e) detecting the labeled antibody; thereby detecting anti-ADAMTS13 antibodies in the test sample.

In another aspect, the invention provides a method for diagnosing TTP in a subject comprising (a) measuring ADAMTS13 activity in a test sample from the subject according to the method of the first or second aspect of the invention; and (b) comparing the ADAMTS13 activity in the test sample to ADAMTS13 activity in a control sample having normal ADAMTS13 activity; wherein TTP is diagnosed by reduced ADAMTS13 activity in the test sample compared with the control sample.

In yet another aspect, the invention provides a method for diagnosing acquired TTP in a subject comprising (a) incubating a sample comprising ADAMTS13 with plasma from the subject; and (b) measuring ADAMTS13 activity in the sample according to the method of the first or second aspect of the invention; wherein acquired TTP is diagnosed by reduced ADAMTS13 activity in the sample compared with ADAMTS13 activity in a control sample having normal ADAMTS13 activity.

The invention additionally provides a method for monitoring treatment of a patient with TTP comprising measuring ADAMTS13 activity according to the first or second aspect of the invention during treatment of the patient.

BRIEF DESCRIPTION OF THE DRAWINGS

The present invention will now be described by way of example, in which reference will be made to the following Figures in which:

FIG. 10A shows platelet proteins electrophoresed using reducing conditions (lanes A and B) and non-reducing conditions (lanes C and D). Lanes A and C were stained with goat anti-PAI-1 antibody as a control; Lanes B and D were stained with goat anti-ADAMTS13 antibody; Lane E contains molecular weight standards. Arrows on the left indicate protein bands specifically immunostained by anti-ADAMTS13 antibodies. FIG. 10B shows immunostaining of platelet proteins using human antibodies. Lane A: reducing conditions and Ig from a subject with acquired TTP; Lane B: non-reducing conditions and Ig from a subject with acquired TTP; Lane C: non-reducing conditions and Ig from a normal subject (control); Lane D: molecular weight markers.

DETAILED DESCRIPTION

In this disclosure, "comprises", "comprising", "containing", "having" and the like can have the meaning ascribed to them in U.S. Patent law and can mean "includes", "including", and the like. "Consisting essentially of" or "consists essentially of" likewise have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

ADAMTS13

Figure 1:
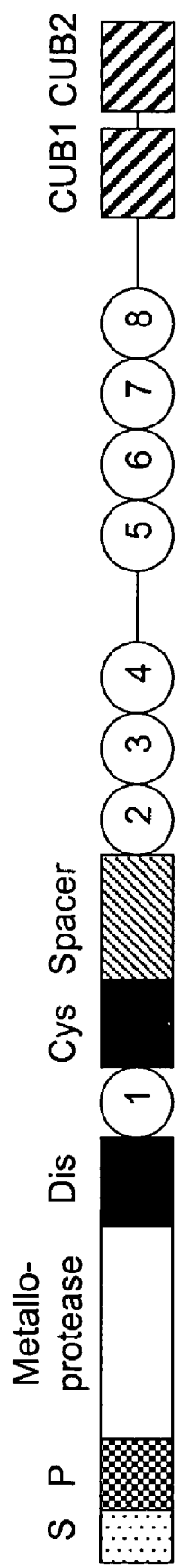
FIG. 1 shows the structure of the plasma form of ADAMTS13. S: signal peptide; P: propeptide; Dis: disintegrin-like region; Cys: Cys-rich region. The catalytic (metalloprotease) region and the two CUB domains are also shown. Thrombospondin type I (TSP1) repeats are shown as numbered circles.

ADAMTS13, also known as von Willebrand factor (VWF)-cleaving protease, is a member of the family of metalloproteases named for the characteristic combination of a disintegrin-like and metalloprotease (reprolysin-type), with thrombospondin type 1 motifs. The structure of plasma ADAMTS13 is shown in FIG. 1. Structural details and sequence information on ADAMTS13 can be found in Zheng et al. (2001; J. Biol. Chem. 276(44):41059-41063). ADAMTS13 cleaves VWF at the Tyr$^{1605}$-Met$^{1606}$ bond and requires both calcium and zinc ions to function.

Until the instant invention, ADAMTS13 activity was primarily studied in plasma. This form of ADAMTS13 is referred to herein as "plasma ADAMTS13". A novel form of ADAMTS13 has now been discovered on platelets and is referred to herein as "platelet ADAMTS13". "Recombinant ADAMTS13" can also be made using standard molecular biology techniques, such as those found in Sambrook, et al., Molecular Cloning, A Laboratory Manual (1989) and Ausubel et al., Short Protocols in Molecular Biology (1999) 4$^{th}$ Ed., John Wiley & Sons, Inc. (as well as the complete version of Current Protocols in Molecular Biology).

Therefore, the invention provides an ADAMTS13 protein and ADAMTS13 activity in platelets. This protein appears to be distinct from plasma ADAMTS13 in that plasma ADAMTS13 is one contiguous polypeptide, whereas platelet ADAMTS13 protein is cleaved into more than one polypeptide, which is then held together by disulfide bonds. Polypeptides of about 120 kD, about 84 kD, about 60 kD, about 43 kD and about 30 kD are seen on an SDS-PAGE gel of platelet ADAMTS13. Platelet ADAMTS13 appears to be cleaved by FXIa. Likewise, this form of ADAMTS13 also appears to be distinct from that reported by Suzuki et al. (2004, Biochem. Biophys. Res. Commun. 313:212-216). Unlike the cleaved platelet ADAMTS13 of the instant invention, the ADAMTS13 of Suzuki et al. has a molecular weight of about 220 kD on an SDS-PAGE gel. Moreover, Suzuki et al. report the larger form of ADAMTS13 in platelets, while experiments performed by the current inventors indicate ADAMTS13 activity on the surface of platelets. Without wishing to be bound by theory, it is possible that the platelet ADAMTS13 of the invention has undergone different post-translational modification than that of Suzuki et al., resulting in a cleaved surface protein, rather than a larger cytoplasmic protein.

The assays of the invention can be used to detect platelet ADAMTS13, plasma ADAMTS13 and recombinant ADAMTS13.

Sources of ADAMTS13 for use in the assays and methods of the invention can be platelet rich plasma (PRP), platelet poor plasma (PPP), pooled normal plasma (PNP), isolated platelets, whole blood, tissue culture supernatant or purified ADAMTS13. Methods for making PRP, PPP, isolated platelets and tissue culture supernatant can be found in the Examples section. Purified ADAMTS13 can be made from plasma, platelets or recombinant cells using standard biochemical techniques for protein isolation and purification including, but not limited to, immunoaffinity chromatography, size exclusion chromatography, ion exchange chromatography, immunoprecipitation, and ammonium sulfate precipitation. The term "plasma" can include PRP, PPP and PNP.

As used herein, "normal platelets", "normal plasma", "normal PRP", etc. are derived from individuals who do not have either congenital TTP or acquired TTP. PNP is a mixture of plasma taken from multiple individuals who do not have TTP. Likewise, "TTP platelets", "TTP plasma", "TTP PRP", etc. are derived from individuals who have either congenital TTP or acquired TTP. "Acquired TTP platelets", "acquired TTP plasma", "acquired TTP PRP", etc. are derived from individuals who have the acquired form of TTP.

Measurements of ADAMTS13 activity are made in relation to "normal activity", that is, ADAMTS13 activity in normal platelets, normal plasma, normal PRP, recombinant or purified ADAMTS13 etc. Thus, terms such as "reduced ADAMTS13 activity" or "inhibited ADAMTS13 activity" refer to ADAMTS13 activity relative to activity measured in a normal sample, i.e. normal platelets, normal plasma, normal PRP, recombinant or purified ADAMTS13 etc.

The methods of the invention are applicable to clinical, veterinary and/or research applications.

Substrates

The invention relates to assays for measuring ADAMTS 13 activity. In one such assay, a sample comprising ADAMTS 13 is incubated with a substrate that comprises a peptide moiety and a chromogenic or fluorogenic moiety and the optical density or fluorescence of the sample is measured, thereby measuring ADAMTS13 activity. In this embodiment, the peptide moiety comprises X-Val-Tyr, X-Leu-Tyr or X-Ile-Tyr, wherein X is any amino acid. In a preferred embodiment, X is Leu. In other preferred embodiments, the peptide moiety is Leu-Val-Tyr, Leu-Leu-Val-Tyr (SEQ ID NO: 2) or Suc-Leu-Leu-Val-Tyr (SEQ ID NO: 2).

The skilled artisan can make amino acid substitutions in the peptide moiety without undue experimentation. For example, amino acid substitutions may be made on the basis of similarity in polarity, charge, solubility, hydrophobicity, hydrophilicity, and/or the amphipathic nature of the residues as long as the binding activity of the substrate is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example, according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Preferably, the peptide moiety is at least about 3 amino acid residues in length. More preferably, the peptide moiety is in the range of about 3 to about 20 amino acid residues in length. Non-conventional amino acids such as those found in the Spectrozyme series of peptidyl substrates from American Diagnostica Inc. (Stamford, Conn.) may also be used to substitute for conventional amino acids, provided that the peptide retains its ability to bind to and be cleaved by ADAMTS13.

Chromogenic moieties suitable for use in the invention include s-benzyl, 5-amino-2-nitrobenzoic acid and 6-amino-1-naphthalenesulfonamides. The chromogenic moiety is not para-nitroanaline (pNA), which has been demonstrated to be an ineffective moiety for an ADAMTS13 substrate. Without wishing to be bound by theory, it is possible that the structure of pNA creates a steric hindrance that prevents ADAMTS13 activity.

Fluorogenic moieties suitable for use in the invention include coumarins, fluoresceins, rhodamines, resorufins and dimethylacridinones. In a preferred embodiment, the fluorogenic moiety is a coumarin. In a particularly preferred embodiment, the coumarin is 7-amino-4-methylcoumarin (AMC).

Another assay provided by the invention is a method for measuring ADAMTS13 activity by incubating a sample comprising ADAMTS13 with a substrate having donor and acceptor moieties that mediate fluorescence resonance energy transfer (FRET). In addition to the donor and acceptor moieties, the substrate comprises a peptide moiety that comprises Val-Tyr-Met, Leu-Tyr-Met or Ile-Tyr-Met. ADAMTS13 activity is determined by measuring the fluorescence of the sample.

FRET is a distance-dependent interaction between the electronic excited states of two dye molecules in which excitation is transferred from a donor moiety to an acceptor moiety without emission of a photon. This is accomplished by using donor/acceptor pairs in which the emission spectrum of the donor overlaps the absorption spectrum of the acceptor. When the two are in spatial proximity, the excitation energy of the donor is transferred to the acceptor through long-range dipole-dipole interactions. When energy transfer occurs, the acceptor quenches the fluorescence of the donor, and thus, the acceptor moiety is also called a quencher. The donor and acceptor moieties must be within about 100 angstroms or 10 nm of one another for efficient energy transfer.

Suitable donor/acceptor pairs for use in FRET are well known in the art. Examples of donor/acceptor pairs can be found in Table 1. It should be noted that Table 1 does not contain an exhaustive list of FRET donor/acceptor pairs, and that the skilled artisan can choose a donor/acceptor pair based on his or her knowledge of the art.

TABLE 1

FRET Donor and Acceptor Moieties

| Donor | Acceptor |
|---|---|
| 7-Methoxycoumarin | DABCYL |
| Amino Methyl Coumarin | DABCYL, QSY-35[1] |
| Blue Fluorescent Protein | Ds Red Fluorescent Protein |
| BODIPY-FL[2] | DABCYL, QSY-7, QSY-9, BHQ-1[3] |
| B-Phycoerythrin | Cy5 |
| Carboxyfluorescein Succinimidyl Ester | Texas Red |
| Cascade Blue | DABCYL |
| Coumarin | DABCYL |
| Cy3 | Cy5, QSY-7, QSY-9, BHQ-2 |
| Cy5 | Cy5.5, QSY-35, BHQ-2 |
| Dansyl | FITC |
| Dansyl | Octadecylrhodamine |
| Dialkylaminocoumarin | DABCYL, QSY-35 |
| EDANS[4] | DABCYL |
| FITC | Eosin Thiosemicarbazide |
| Fluorescein | Tetramethylrhodamine |
| Green Fluorescent Protein | Yellow Fluorescent Protein |
| IAEDANS[5] | DDPM[6] |
| Marina Blue | DABCYL, QSY-35 |
| Pacific Blue | DABCYL, QSY-35 |
| Rhodamine 6G | Malachite Green |
| Tryptophan | Dansyl |

[1]QSY quenchers are analogs of fluorescein.
[2]4,4-difluoro-4-bora-3a,4a-diaza-s-indacene
[3]Black Hole Quenchers ™ by Biosearch Technologies, Inc., Novato, CA
[4]5-[(2-aminoethyl)amino]naphthalene-1-sulfonic acid
[5]5-(2-iodoacetylaminoethyl)aminonaphthalene-1-sulfonic acid
[6]N-(4-dimethylamino-3,5-dinitrophenyl)maleimide The preferred donor/acceptor pair is EDANS/DABCYL.

Preferably, the peptide moiety is at least about 3 amino acid residues in length. More preferably, the peptide moiety is in the range of about 3 to about 30 amino acid residues in length. Advantageously, the peptide moiety is Asn-Leu-Val-Tyr-Met-Val-Thr-Gly-Asp (SEQ ID NO: 3). Amino acid substitutions can be made as described above without departing from the spirit and scope of the invention.

The preferred substrate for use in this embodiment of the invention is $NH_2$-Arg-Lys-(DABCYL)-Asn-Leu-Val-Tyr-Met-Val-Thr-Gly-Asp-(EDANS)-Arg-COOH (SEQ ID NO: 1).

Methods for making the ADAMTS13 substrates of the invention are also contemplated. Said methods comprise covalently linking a peptide moiety, as described above, to a chromogenic or fluorogenic moiety, or to a donor moiety and an acceptor moiety that mediate FRET, using well known synthesis techniques.

Inhibitors of ADAMTS13

An embodiment of the invention involves a method for inhibiting ADAMTS13 using an inhibitory antibody against ADAMTS13. Several anti-ADAMTS13 antibodies are available from various sources. For instance, Examples 12 and 14 demonstrate the inhibitory effects of anti-ADAMTS13 antibodies from goat, rabbit and human.

Autoantibodies that inhibit ADAMTS13 activity can be detected in subjects with acquired TTP. (See Klaus et al. 2004, Blood 103(12):4514-4519.) These antibodies can be isolated from the plasma of acquired TTP patients and used in vitro as inhibitors of ADAMTS13. Moreover, a method of diagnosing acquired TTP provided by the instant invention is to incubate an ADAMTS13 sample with plasma from a subject to be tested for acquired TTP and to measure ADAMTS13 activity using one of the assays of the invention. Inhibition of ADAMTS13 activity by the plasma indicates the presence of inhibitory anti-ADAMTS13 antibodies in the plasma, and thus confirms a diagnosis of acquired TTP.

Klaus et al. (Ibid) performed epitope mapping experiments in order to deduce the nature of inhibitory ADAMTS13 antibodies in patients with acquired TTP. The results indicate that antibodies directed against the cysteine rich/spacer domain of ADAMTS13 were detected in all cases. In addition, antibodies directed against the TSP1-1 repeat or a fragment containing the TSP1-1 repeat, the disintegrin-like domain and the catalytic domain were detected in 72% of patients. Further, antibodies directed against the CUB 1 and/or CUB 2 domains were detected in 64% of patients. For purposes of this invention, the C-terminus consists of thrombospondin type 1 TSP1 repeats 2-8 and the CUB domains. FIG. 1 shows a schematic diagram of ADAMTS13.

The invention provides a method for identifying inhibitors of ADAMTS13. The inhibitor can be, inter alia, a polypeptide, a peptide, an oligonucleotide, a polynucleotide, a nucleoside or nucleoside analog, a saccharide, a small molecule, or a natural or synthetic chemical. The method comprises incubating a sample of ADAMTS13 with a candidate inhibitor and measuring ADAMTS13 activity according to one or more of the assays provided by the invention. The inhibitor is identified by reduced ADAMTS13 activity in the test sample, compared with ADAMTS13 activity in a control sample not incubated with the candidate inhibitor. The candidate inhibitor can be generated using known techniques, and can be derived, for example, from a chemical compound library, a phage display library, a natural chemical library or a combinatorial chemistry library.

ELISA

The Enzyme Linked Immunosorbent Assay (ELISA) is a solid-phase immunoassay that is widely used in both clinical and basic research settings. In one type of ELISA, an antigen is attached to the solid phase, which is most commonly a membrane, plate, microwell or bead. The solid phase is then incubated with an antibody to the antigen (a "primary antibody"). If the primary antibody is conjugated to a label, it can be detected. This process is known as direct immunolabelling. Alternatively, the primary antibody may be unlabelled, in which case an antibody to the primary antibody (a "secondary antibody"), raised in a different species from the primary antibody and conjugated to a label, is incubated with the solid phase. This detection method is referred to as indirect immunolabelling. Immunolabelling methods are well known in the art.

In a different type of ELISA, an antibody is attached to the solid phase. This antibody can then be used to capture an antigen of interest. Direct or indirect immunolabelling techniques can be employed for the sake of analysis. In the instant invention, ADAMTS13 in a sample can be measured by binding an anti-ADAMTS13 antibody to a solid phase and adding the sample to the solid phase. ADAMTS13 present in the sample binds to the antibody, and bound ADAMTS13 is detected using direct or indirect immunolabelling. The amount of ADAMTS13 in the sample can be measured by quantifying the label.

In a preferred embodiment, the sample is or comprises platelets. In another preferred embodiment, the sample is plasma.

Another ELISA provided by the invention is used to detect anti-ADAMTS13 antibodies in a test sample. In this embodiment, an anti-ADAMTS13 antibody raised in a first species, e.g. a goat, is bound to a solid phase. ADAMTS13 is added and binds to the antibody raised in the first species. A test sample from a second species, e.g. human, is added, and any anti-ADAMTS13 antibodies present in the test sample bind to the ADAMTS13. Finally, a labelled antibody against antibodies from the second species is added. The labelled antibody is raised in a third species, e.g. donkey, and binds to the antibody from the second species. By detecting the label, one can detect anti-ADAMTS13 antibodies in the test sample.

The test sample can be any biological fluid, such as blood, plasma, serum, culture fluid, cerebralspinal fluid or sputum. In a preferred embodiment, the biological fluid is plasma.

The label can be any moiety known in the art, including chromogenic enzyme systems, such as horseradish peroxidase, alkaline phosphatase, $\beta$-galactosidase, glucose 6-phosphate dehydrogenase. These enzyme labels are reacted with a chromogenic substrate that can be detected by conventional techniques. In a preferred embodiment, the label is horse radish peroxidase, and the substrate is tetramethylbenzidine. The label can also be a fluorescent dye, including rhodamine, fluorescein, Cy dyes, Texas Red, and derivatives thereof.

Diagnostic Applications

In addition to the method discussed above for diagnosing acquired TTP by testing the inhibitory properties of plasma on an ADAMTS13 sample, the invention provides other methods for the diagnosis of both congenital and acquired TTP.

For example, congenital or acquired TTP can be diagnosed by measuring ADAMTS13 activity in a test sample from a subject using one of the assays of the invention and subsequently comparing the ADAMTS13 activity in the test sample to ADAMTS13 activity in a control sample having normal ADAMTS13 activity. Reduced ADAMTS13 activity in the test sample compared with the control sample indicates a positive diagnosis of TTP.

Acquired TTP can be diagnosed in a subject by incubating a sample comprising ADAMTS13 with plasma from the subject; and measuring ADAMTS13 activity in the sample using one of the assays of the invention. Reduced ADAMTS13 activity in the sample, compared with ADAMTS13 activity in a control sample having normal ADAMTS13 activity, indicates acquired TTP.

Treatment Applications

The techniques provided by the invention can be used to monitor treatment of a patient for TTP. For example, during treatment, ADAMTS13 activity can be measured using the assays of the invention. This allows the clinician to assess the efficacy of the treatment and/or to determine the length of a treatment session that is required to restore ADAMTS13 activity.

One treatment for TTP is plasmaphoresis. In patients with acquired TTP, plasmaphoresis is used to remove the inhibitory anti-ADAMTS13 antibodies from the patient's plasma. Replacement of the deficient ADAMTS13 is provided by infused plasma. Recent advances in our understanding of the pathological mechanisms of TTP provide a rationale for monitoring plasmaphoreseis via measuring the levels of ADAMTS13 activity in the patient undergoing plasmaphoresis.

Because the platelet form of ADAMTS13 reacts with low molecular weight substrates more efficiently than the plasma form, platelet ADAMTS13 is likely to be a better target for drugs designed to treat TTP. Therefore, the invention provides a method for treating TTP in a patient in need thereof comprising administering to the patient a drug that specifically targets platelet ADAMTS13. The drug can be identified using the screening methods provided by the invention and described herein. The term "drug" is meant to encompass a polypeptide, a peptide, an oligonucleotide, a polynucleotide or vector containing a polynucleotide, a nucleoside or nucleoside analog, a saccharide, a small molecule, or a natural or synthetic chemical.

The invention will now be further described by way of the following non-limiting Examples, given by way of illustration.

EXAMPLES

Materials and Methods

Synthetic Peptidyl Substrates

Leu-Val-Tyr-AMC (LVY-AMC) and Suc-Leu-Leu-Val-Tyr-AMC (Suc-LLVY-AMC) (SEQ ID NO: 2) were obtained from Bachem Bioscience Inc. (King of Prussia, Pa.). LVY-AMC was also made by QPR (Montreal, Canada). FRET substrate, $NH_2$-Arg-Lys(DABCYL)-NLVYMVTGD (EDANS)-Arg-COOH (SEQ ID NO: 1), was made for American Diagnostica Inc. by Molecular Biology-Resource Center, University of Oklahoma Health Sciences Center (Oklahoma City, Okla.).

Preparation of Platelet Rich Plasma (PRP), Platelet Poor Plasma (PPP) and Isolated Platelets Blood was collected by venopuncture into collection tubes containing 0.12 M sodium citrate, an anti-coagulant. The citrated blood was centrifuged at 700 rpm for 10 minutes. The supernatant was removed and saved as the platelet rich plasma (PRP) fraction. The PRP was centrifuged at 10,000 rpm for 20 minutes. The supernatant was removed and saved as the platelet poor plasma (PPP) fraction. The pellet contained the platelets, which were washed by resuspending in 10 mM Tris-HCl pH 8.0 buffer and centrifuging at 10,000 rpm for 10 minutes. The isolated platelets were resuspended in buffer and used in experiments.

Recombinant ADAMTS13

HEK 293 cells were transfected with a vector encoding ADAMTS13. Cell culture supernatant from the transfected HEK 293 cells, containing recombinant ADAMTS13, was generously provided by Dr. David Ginsburg (University of Michigan, Mich.). Mock transfected cell supernatant with no recombinant ADAMTS13 was also provided as a control.

Example 1

Figure 2:
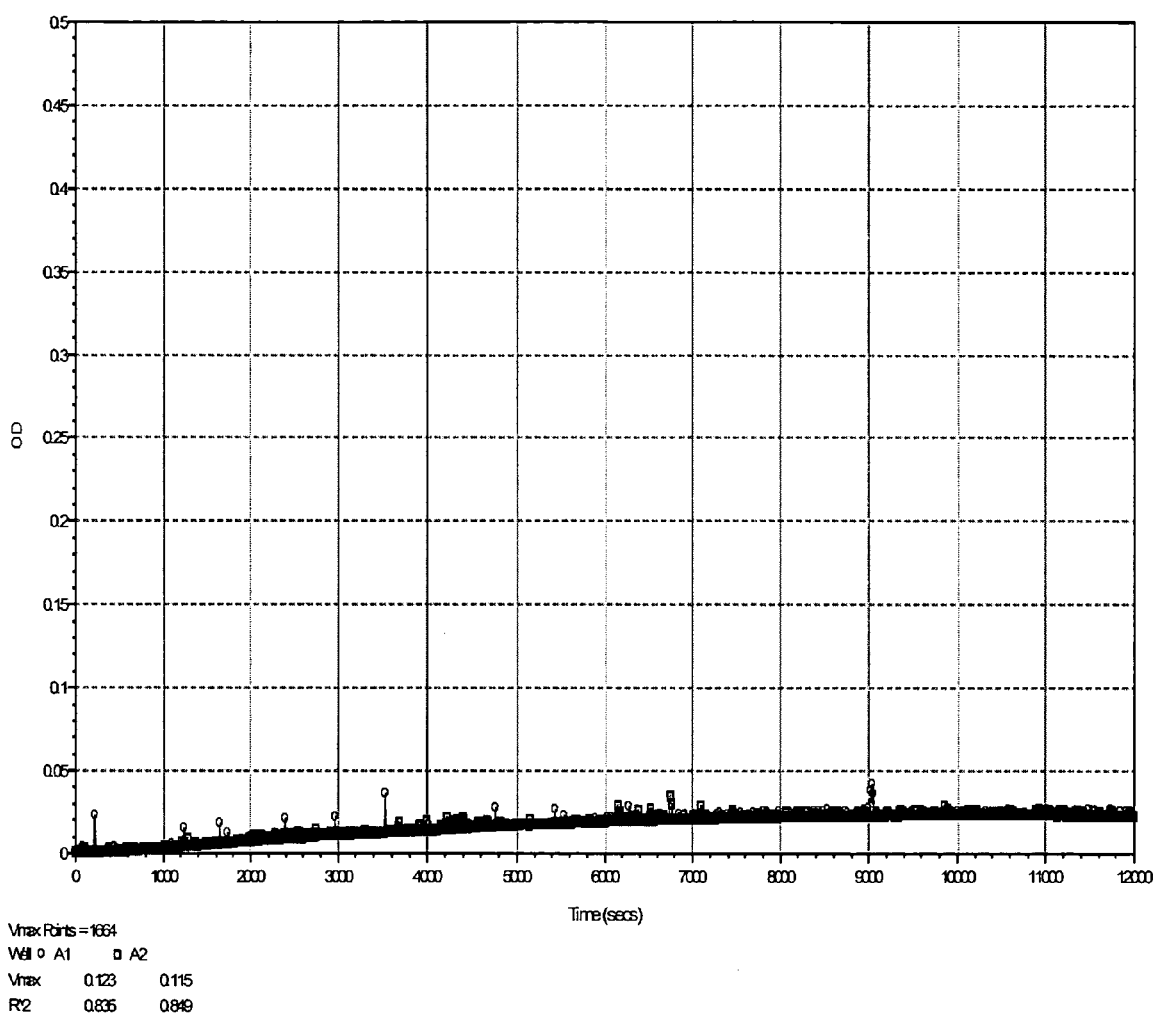
FIG. 2 shows LVY-pNA as a substrate for ADAMTS13.

Measurement of ADAMTS13 Activity in PRP Using LVY-pNA and LVY-AMC Peptidyl Substrates As discussed above, Furlan et al. reported that some peptidyl-pNA moieties, such as XLY-pNA and XVY-pNA, were not substrates for ADAMTS13. We prepared LVY-pNA and tested it for its ability to be cleaved by ADAMTS13. The results shown in FIG. 2 confirm the findings of Furlan et al., i.e., LVY-pNA was not cleaved by ADAMTS13.

Thus, the nature of the leaving group of the peptidyl substrate appears to be important in determining the ability of ADAMTS13 to cleave a chromophor or a fluorophor from the end of a peptidyl substrate.

Example 2

Figure 3:
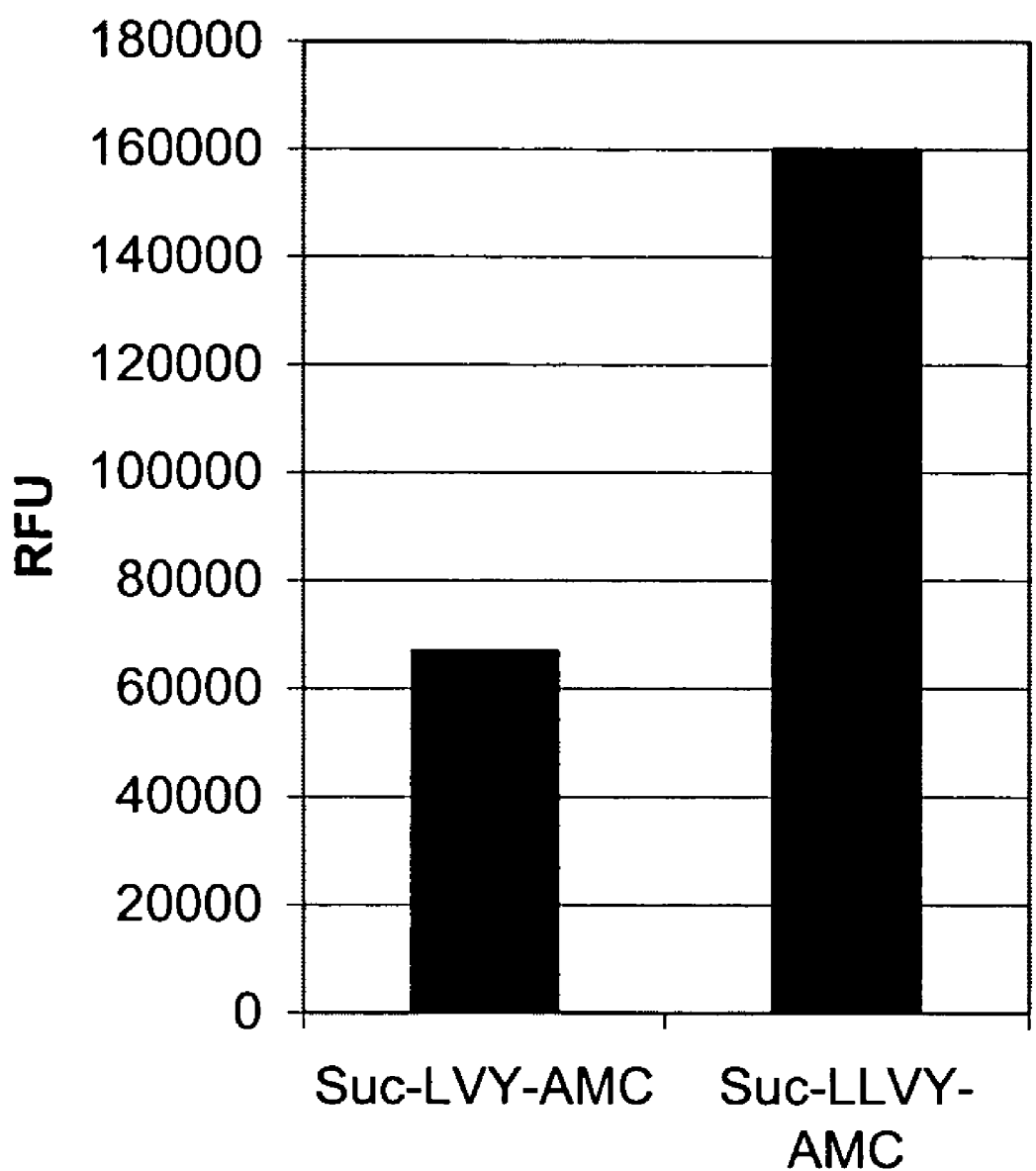
FIG. 3 shows a comparison of LVY-AMC and Suc-LLVY-AMC (SEQ ID NO: 2) substrates for measuring ADAMTS 13 activity.

Measurement of ADAMTS13 Activity in PRP Using Peptidyl Substrates of Different Lengths In order to determine the effect of modifying the length of the peptide sequence conjugated to the AMC fluorochrome, normal PRP (20 µl) was incubated at 37° C. with a final concentration of 0.8 mM Suc-LLVY-AMC (SEQ ID NO: 2) or LVY-AMC in 10 mM Tris-HCl pH 8.0 buffer in total volume of 200 µl. Fluorescence was measured using a microtiter fluorophotometric plate reader (Ex 360 nm/Em 460 nm). Both peptidyl-AMC substrates were cleaved by ADAMTS13 in PRP, with the Suc-LLVY-AMC (SEQ ID NO: 2) giving a higher signal over time as compared to the LVY-AMC substrate (FIG. 3).

This example demonstrates that different ADAMTS13 substrates can be made by altering the peptide sequence that is conjugated to the AMC fluorophor.

Example 3

Measurement of ADAMTS13 Activity Using a FRET Substrate

ADAMTS 13 activity was measured using a fluorescent substrate attached to a donor moiety and an acceptor moiety that functions by fluorescence resonance energy transfer (FRET). The ADAMTS 13 selective substrate, $NH_2$-Arg-Lys(DABCYL)-NLVYMVTGD(EDANS)-Arg-COOH (SEQ ID NO: 1), was used in this example. The NLVYMVTGD peptide sequence (SEQ ID NO: 3) of this substrate is homologous to the ADAMTS 13 cleavage site on VWF. The intact peptidyl substrate has low fluorescence, due to quenching of the DABCYL-fluorochrome by the EDANS-quencher. Cleavage of the substrate between the tyrosine and methionine of the peptide sequence results in an increase in fluorescence.

Figure 4:
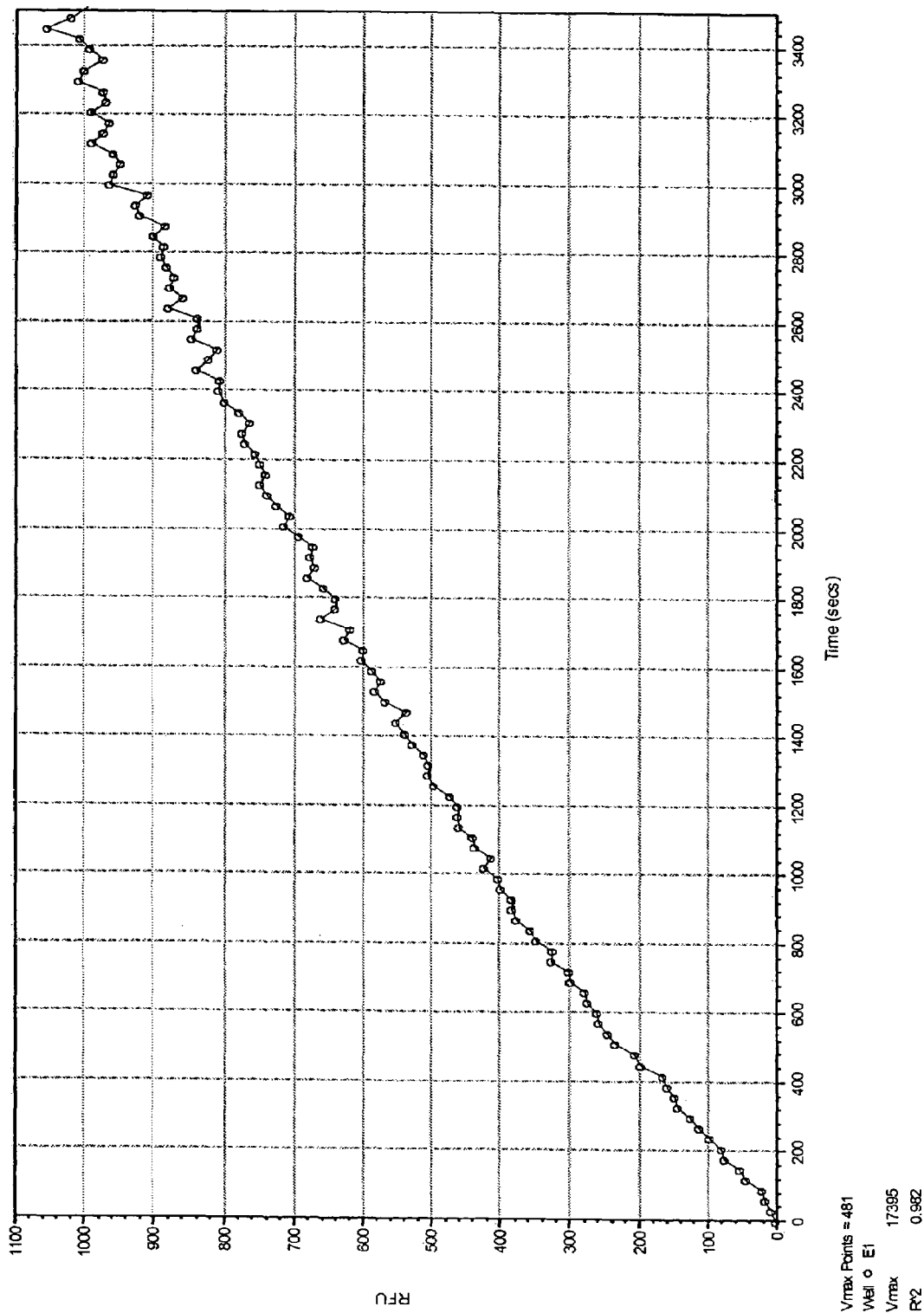
FIG. 4 shows the measurement of cleavage of an ADAMTS 13 substrate using fluorescence resonance energy transfer (FRET). The substrate, $NH_2$-Arg-Lys(DABCYL)-NLVYMVTGD(EDANS)-Arg-COOH (SEQ ID NO: 1), was incubated with normal platelets, and the increase in fluorescence over time was measured.

Isolated platelets in 10mM Tris-HCl pH 8.0 assay buffer were incubated with a final concentration of 8 µg/ml of the FRET substrate at 37° C. The fluorescence was measured in a spectrofluorometric plate reader (Ex 360 nm/Em 440 nm). FIG. 4 shows that incubation of platelets with $NH_2$-Arg-Lys(DABCYL)-NLVYMVTGD(EDANS)-Arg-COOH (SEQ ID NO: 1) results in increased fluorescence over time, indicating that the form of ADAMTS 13 found on platelets cleaves this FRET peptide substrate. The skilled artisan can design other FRET substrates for measuring ADAMTS13 activity using his or her own knowledge and the teachings herein.

Example 4

Figure 5:
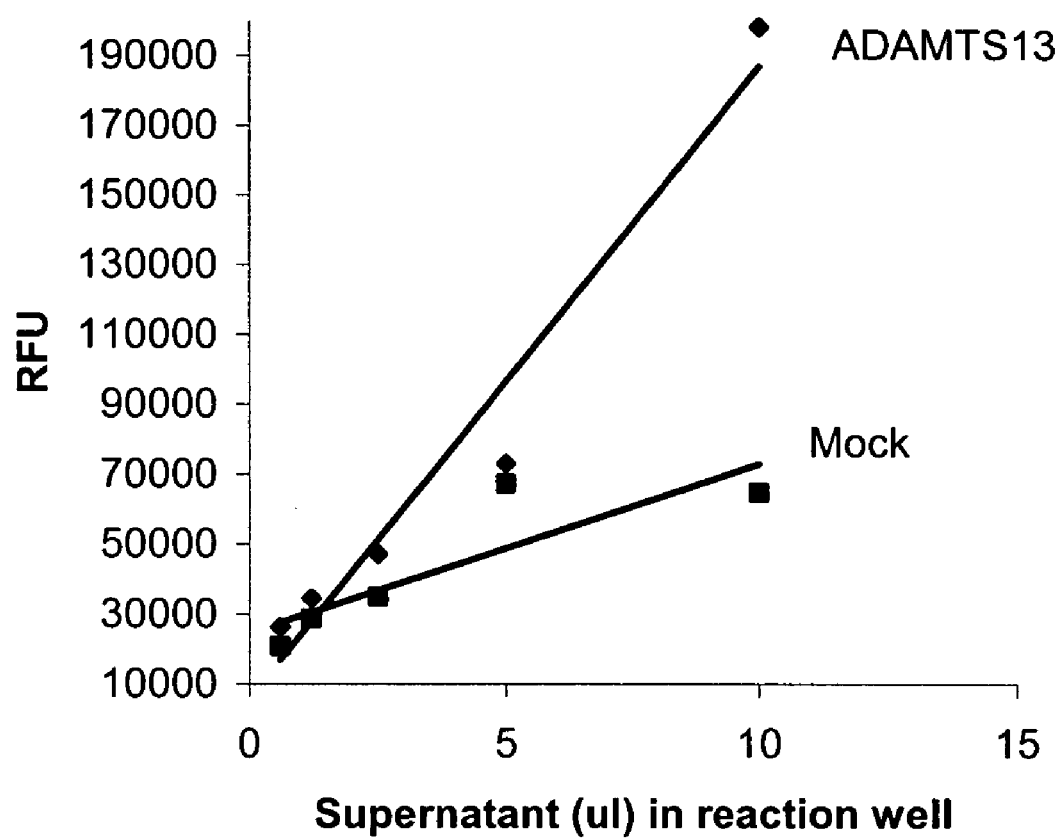
FIG. 5 shows ADAMTS 13 activity in tissue culture fluid from mock transfected and ADAMTS 13 transfected HEK 293 cells. Activity was measured using Suc-LLVY-AMC (SEQ ID NO: 2) fluorescent substrate.

Measurement of Recombinant ADAMTS13 Activity in Tissue Culture Supernatants Using Suc-LLVY-AMC (SEQ ID NO: 2) Fluorescent Substrate Fluorescence signals were compared between tissue culture supernatant from HEK 293 cells transfected with a viral vector coding for recombinant ADAMTS 13 ("recADAMTS 13") and supernatant from mock transfected HEK 293 cells, as a control. (Culture supernatants were supplied by Dr. David Ginsburg, University of Michigan.) Varying amounts of the two culture supernatants were added to 0.8 mM Suc-Leu-Leu-Val-Tyr-AMC (SEQ ID NO: 2) fluorescent substrate in 50 mM Tris-HCl pH 8.0 in a total volume of 100 μl. FIG. 5 shows that a greater fluorescence signal was produced by the supenatant from transfected cells verses supenatant from mock transfected cells. The increased fluorescence signal is due to cleavage of the substrate by recADAMTS 13 in supernatant of the vector transfected cell supernatant.

Example 5

Measurement of ADAMTS13 Activity in Plasma

Figure 6:
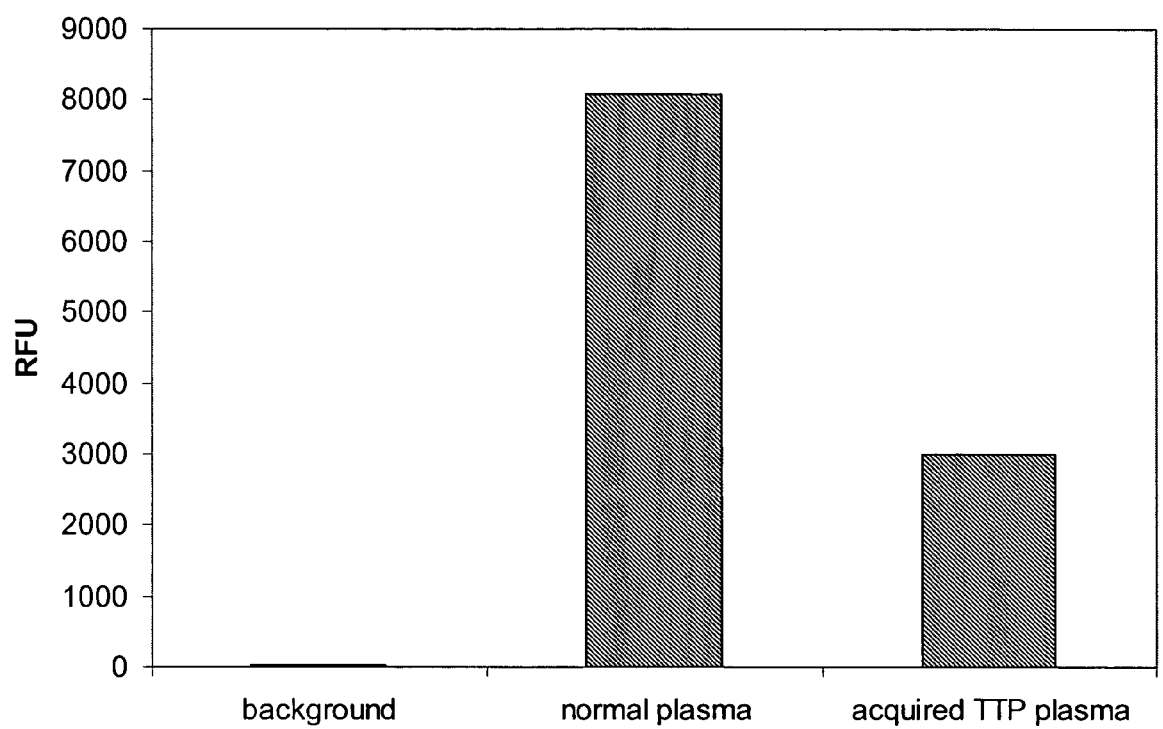
FIG. 6 shows a comparison of ADAMTS 13 activity in plasma from normal subjects and from subjects with acquired TTP using Suc-LLVY-AMC (SEQ ID NO: 2) fluorescent substrate.

ADAMTS13 activity was measured in plasma using the Suc-LLVY-AMC (SEQ ID NO: 2) substrate. Normal plasma (50 μl) or acquired TTP plasma (50 μl) was added to substrate in 50 mM Tris-HCl pH 8.0 buffer. The final concentration of the substrate was 0.8 mM; substrate in buffer was used as a background control. The reaction mixture was incubated at 37° C. for 4 hours and fluorescence was recorded in a spectrofluorometric plate reader at Ex 360 nM/Em 440 nM (FIG. 6). Higher ADAMTS13 activity was observed in the normal plasma as compared to acquired TTP plasma.

Example 6

Comparison of ADAMTS13 Activity in PRP from Normal and TTP Subjects

The ADAMTS13 activity from normal plasma and from acquired TTP plasma were compared in the fluorescence assay described above. Specifically, 20 μl of normal PRP were serially diluted 1:2 in normal PPP in microtiter wells. Eighty μl of LVY-AMC (0.2 mM final concentration) in 10 mM Tris-HCl pH 8.0 buffer were added to the PRP. The microtiter plate was placed in a spectrofluorometric microtiter plate reader at 37° C. and the fluorescence was monitored at Ex 360 nm/Em 440 nm for 16 minutes.

Figure 7:
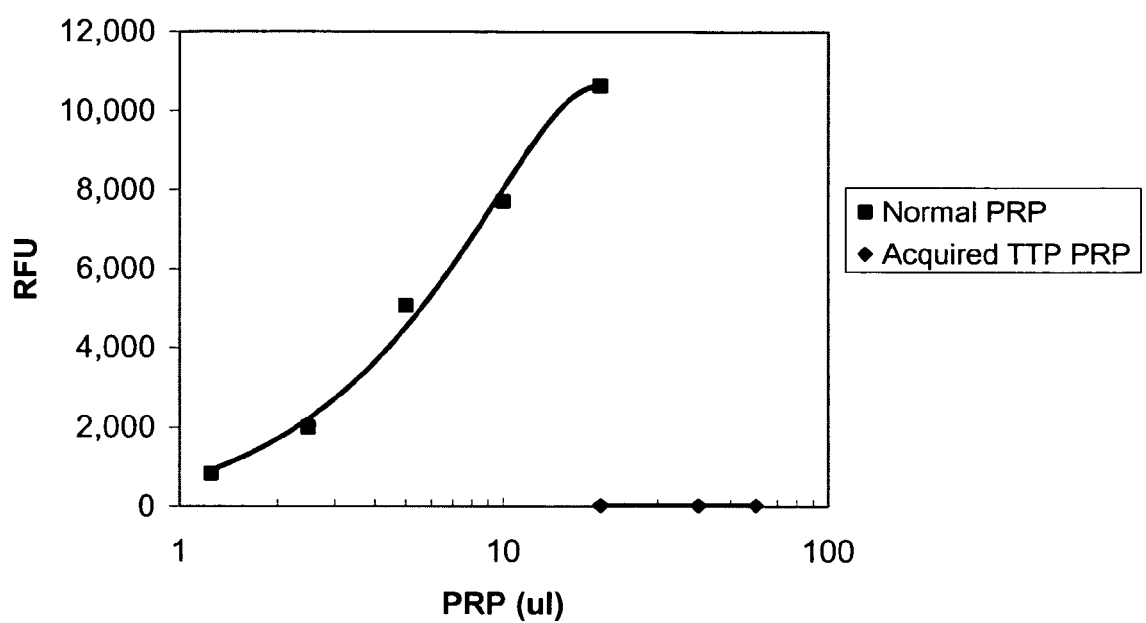
FIG. 7 shows the quantitation of ADAMTS13 activity in PRP from normal subjects (■) and subjects with acquired TTP (♦).

The results shown in FIG. 7 demonstrate that, as the amount of PRP in the assay decreased, there was a decrease in the fluorescence signal. PRP from a patient diagnosed with acquired TTP was tested in the assay under the same conditions as normal PRP. In this experiment, more plasma from the acquired TTP patient (20-60 μl) was used in the assay, as compared to normal PRP. No fluorescent signal was generated at the highest amount of PRP from the acquired TTP patient. This shows that ADAMTS13 activity in PRP from an acquired TTP patient has significantly less activity than normal PRP. This method can be used to diagnose deficiency in ADAMTS13 activity.

Example 7

ADAMTS13 Activity Is Associated with Platelets

Figure 8:
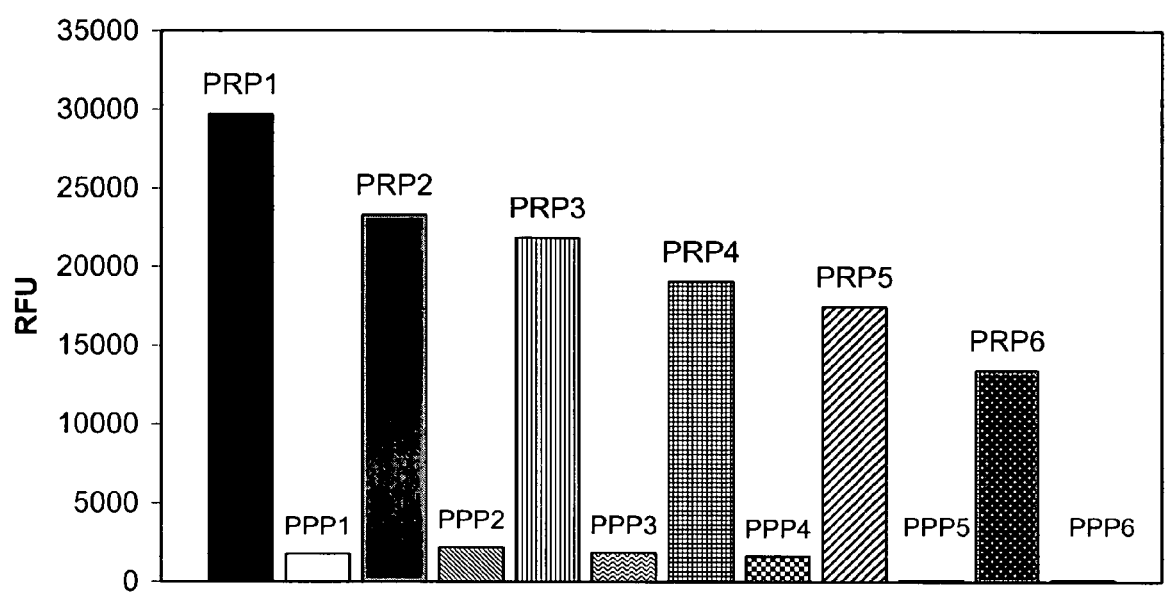
FIG. 8 shows the measurement of ADAMTS 13 activity in platelet rich plasma (PRP) and platelet poor plasma (PPP) from six individual samples taken from normal subjects. ADAMTS 13 activity was measured using Suc-LLVY-AMC (SEQ ID NO: 2) fluorescent substrate.

PRP and PPP from six normal volunteers were prepared as described above. Fifty μl of each plasma sample were added to 130 μl 50mM Tris-HCl buffer pH 8.0 and 20 μl of 8mM Suc-LLVY-AMC substrate (SEQ ID NO: 2). The reaction mixtures were incubated at 37° C. and monitored for 1 hour in a spectrofluormetric plate reader at Ex 360 nm/Em 440 nm. The six PRP samples exhibited high ADAMTS13 activity, as evidenced by generation of a high fluorescence signal (RFU) over time (FIG. 8).

The rate of fluorescence generation over time was significantly greater in PRP than in plasma. After pelleting of platelets, the PPP from each subject was also tested, and exhibited very little ADAMTS13 activity. These results show that the majority of ADAMTS13 activity in PRP is present on the platelets and not in the plasma.

Example 8

Figure 9:
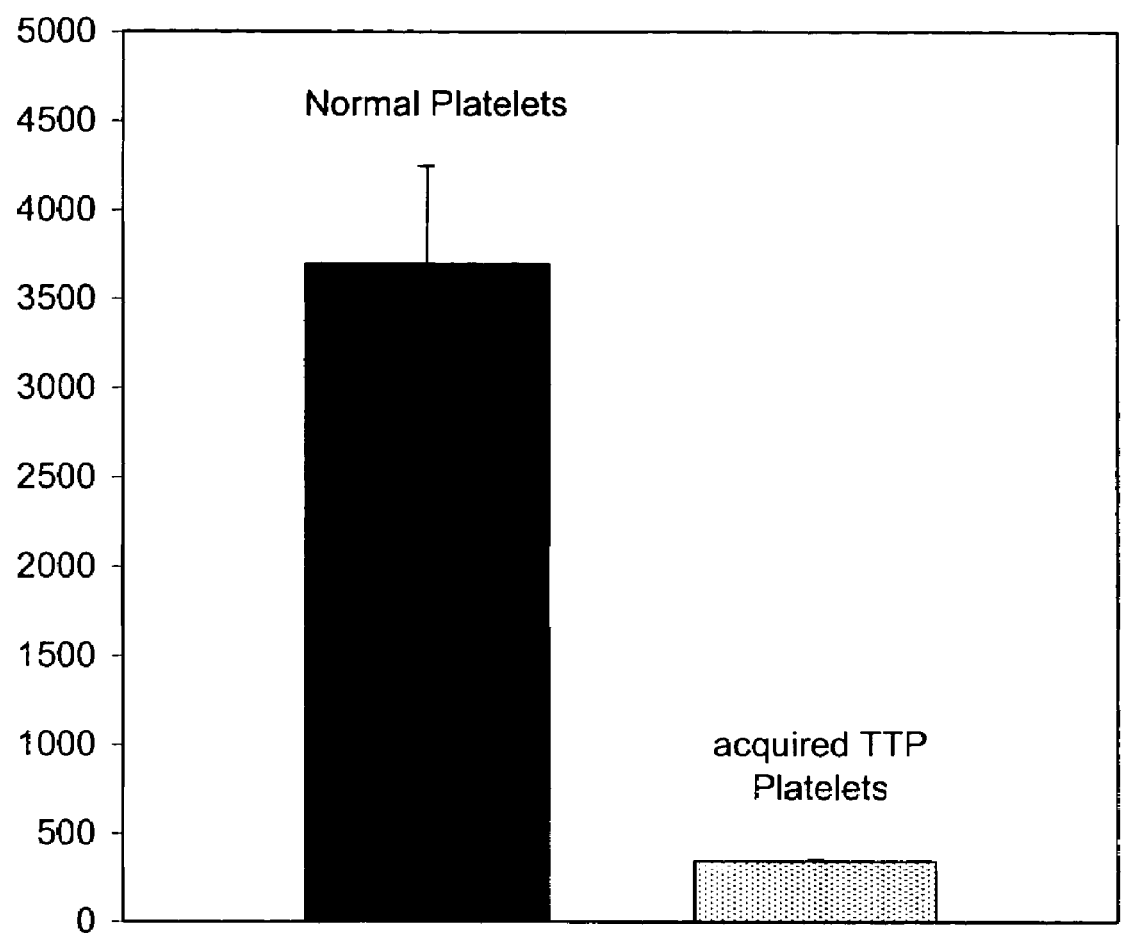
FIG. 9 shows a comparison of ADAMTS13 activity per mg of protein on platelets from normal subjects and subjects with acquired TTP.

Reduced ADAMTS13 Activity is Associated with Human Platelets from an Acquired TTP Patient Isolated platelets from a normal subject and from a patient diagnosed with acquired TTP were prepared as described above. Approximately 600 μg of protein in 100 μl of 50 mM Tris-HCl pH 8.0 buffer from the normal and the acquired isolated platelets were placed in wells in a fluorescence microtiter plate. LVY-AMC substrate was added to each tube to a final concentration of 0.2 mM and the reaction mixtures were incubated at 37° C. for 1 hour. The fluorescence was monitored at Ex 360 nm/Em 440 nm. The amount of ADAMTS13 activity per mg of protein associated with normal platelets was significantly greater than that associated with platelets from a patient with acquired TTP (FIG. 9).

This method can be used to quantitate ADAMTS13 activity on platelets. Low ADAMTS13 activity would indicate TTP. Both congenital TTP, caused by mutation or alteration of ADAMTS13, and acquired TTP, caused by presence of ADAMTS13 inhibitory antibodies, can be diagnosed using this method.

Example 9

ADAMTS13 Associated with Platelets is Present in a Cleaved Form

Figure 10:
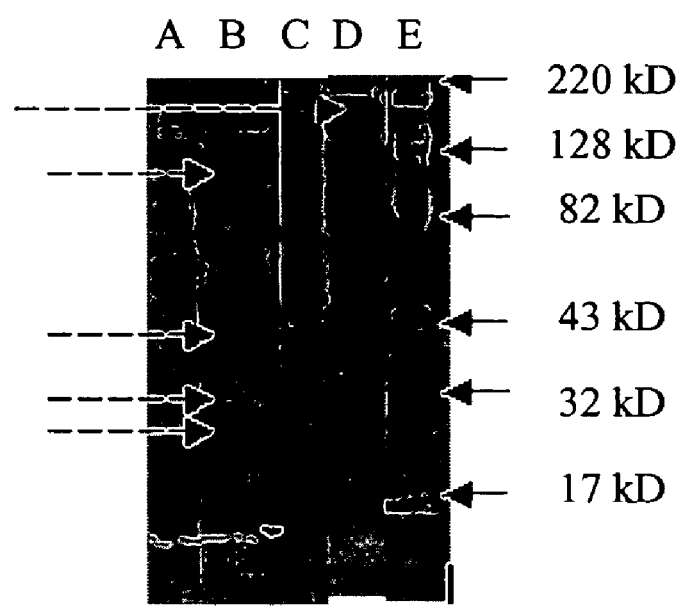
FIG. 10 shows immunostaining Western blots of platelet proteins by various anti-ADAMTS13 antibodies.
Figure 10:
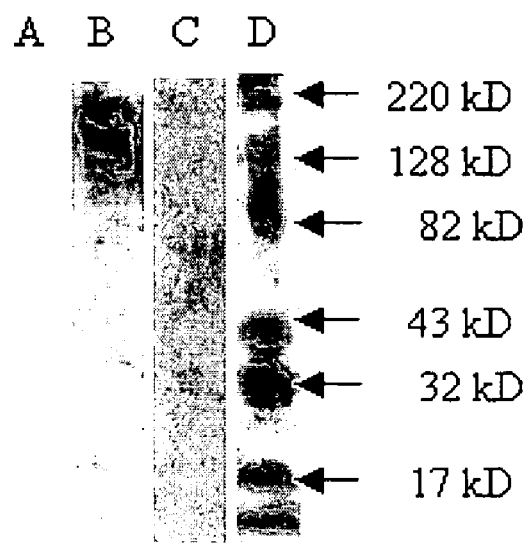

The molecular form of ADAMTS13 in platelets was investigated by immunostaining of Western blots of platelet proteins (FIG. 10). Washed platelets were solubilized in SDS-sample buffer with and without mercaptoethanol. SDS-PAGE electrophoresis was performed using 4-20% acrylamide gel. The resolved proteins were electroblotted onto nylon paper and immunostained with different biotinylated anti-ADAMTS13 antibodies and strepavidin-HRP/TMB. A goat anti-ADAMTS13 antibody specifically immunostained protein bands under reducing conditions at approximately 120 kD, 43 kD and 30 kD. Using non-reducing conditions, a high molecular weight band at approximately 150 kD was specifically immunostained.

These findings suggest that ADAMTS13 on platelets is comprised of more than one protein held together by disulfide bonds. ADAMTS13 in plasma has been reported to be comprised of a single protein of molecular weight 150-170 kD. The ADAMTS13 associated with platelets is different than plasma ADAMTS13, and appears to be cleaved. ADAMTS13 from platelets was immunostained using plasma from an acquired TTP patient. A high molecular weight band was specifically immunostained under non-reducing conditions. Reduction of the protein caused the ADAMTS13 not to be stained by this TTP plasma.

Example 10

Enhanced Activity of Platelet ADAMTS13 by Treatment with a Proteolytic Enzyme

ADAMTS13 on platelets appears to be proteolytically cleaved into at least two or more polypeptide chains held together by disulfide bonds, whereas plamsa ADAMTS13 is a single peptide chain. We tested whether a peptidase can cleave ADAMTS13 and increase activity toward ADAMTS13 peptide substrates.

Figure 11:
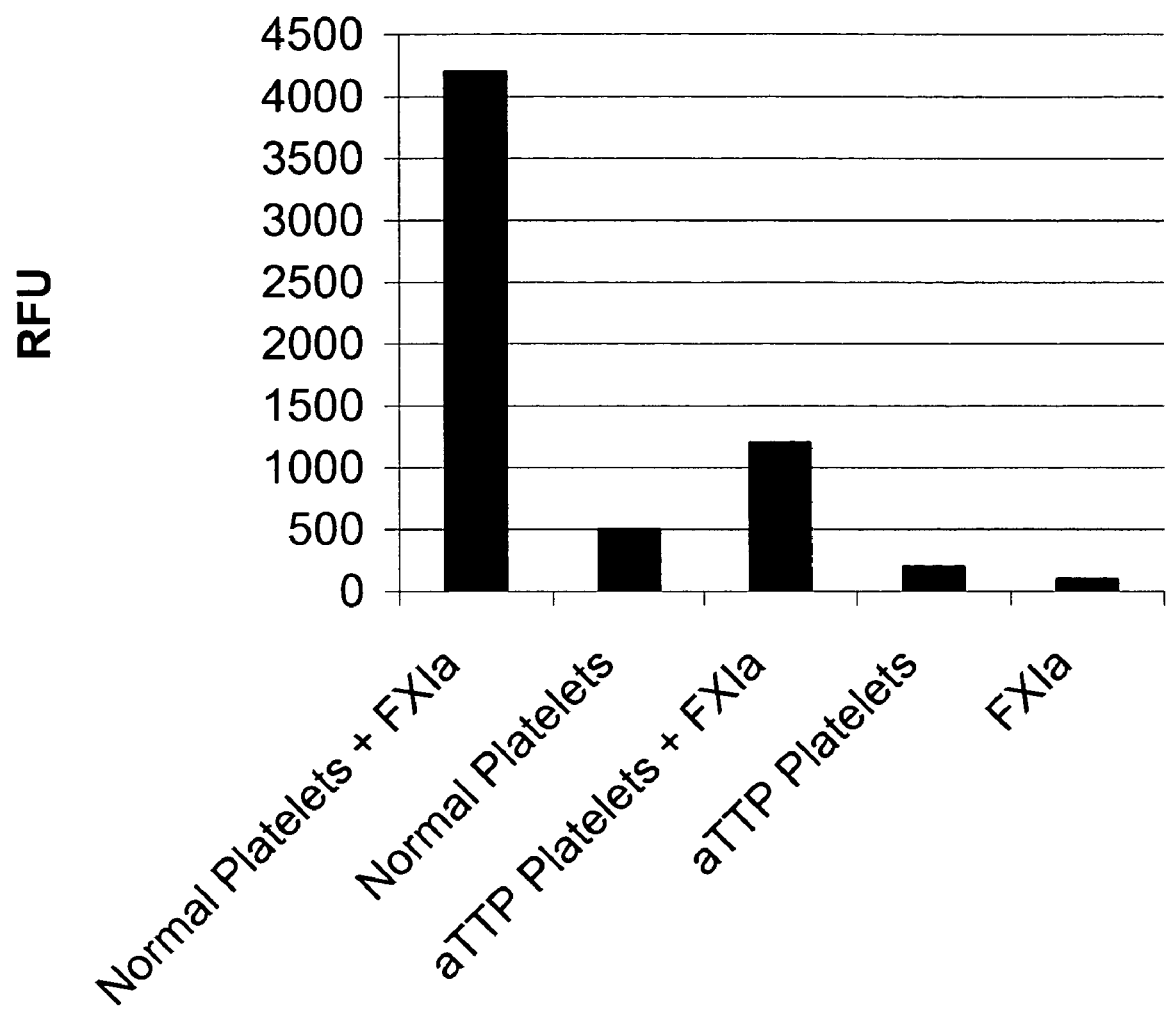
FIG. 11 shows that ADAMTS13 activity on normal platelets and on platelets from a subject with acquired TTP is enhanced by treatment with the peptidase activated Factor XIa (FXIa).

FIG. 11 shows that ADAMTS13 activity on platelets is enhanced by treatment with peptidase activated FXIa. Washed normal platelets from 200 µL of PRP were resuspended in 1 ml of assay buffer. Washed platelets from 1 ml of PRP from a subject with acquired TTP were resuspended in 50 µL of assay buffer. Normal or TTP platelets (10 µl) were added to 10 mM Tris-HCl pH 8.0 assay buffer (80 µl) or assay buffer containing 0.3 ng/ml of FXIa (80 µl). LVY-AMC substrate (10 µl of 2 mM) was added and the fluorescence was monitored (Ex 360 nm/Em 440 nm) for 1500 seconds. FXIa at 0.3 ng/ml was used as a control. ADAMTS13 activity was significantly increased (by approximately 8-fold) towards LVY-AMC substrate upon treatment of platelets with FXIa. Activity of platelets isolated from PRP of an acquired TTP patient was enhanced by treatment with FXIa to a much lesser extent than those isolated from PRP of a normal individual. This shows that the inhibitory antibodies in TTP plasma block activation of platelet ADAMTS13 by FXIa.

Figure 12:
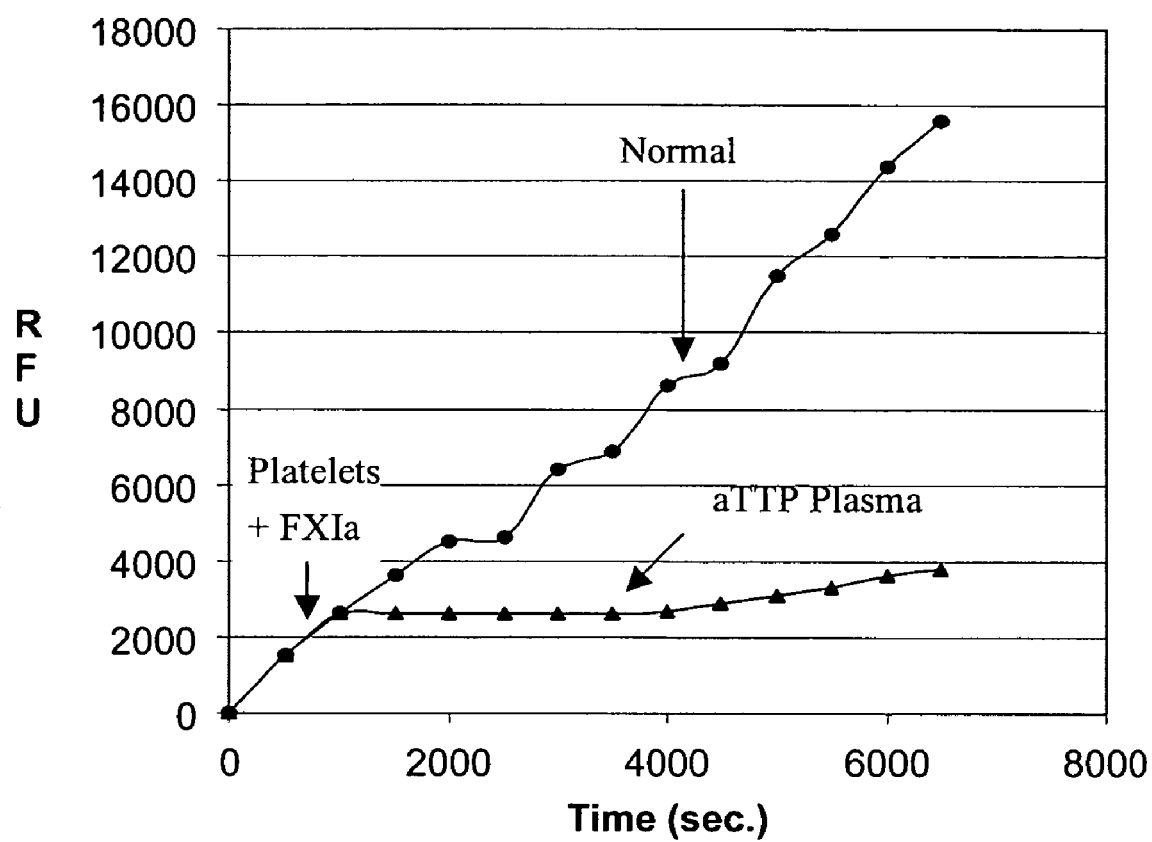
FIG. 12 shows a plot of FXIa activated platelet ADAMTS13 activity in normal plasma, and its inhibition by plasma from a subject with acquired TTP.

The activity of FXIa treated platelets towards LVY-AMC was significantly reduced after addition at 1500 seconds of 50 µl acquired TTP plasma to the reaction mixture, whereas, addition of 50 µl normal plasma had no significant effect on the activity (FIG. 12). These results show that the enhancement of platlelet ADAMTS13 activity by FXIa is blocked by anti-ADAMTS13 antibodies. These findings also show that ADAMTS13 activity can be enhanced by treatment with proteolytic enzymes.

These findings suggest that ADAMTS13 present on platelets is in a different form than that found in plasma. Results above show that platelet ADAMTS13 appears to have greater enzymatic activity towards peptidyl substrates than plasma ADAMTS13. The finding of proteolytically cleaved ADAMTS13 on platelets may explain the differences in reactivity of plasma and platelet-bound ADAMTS13 towards peptidyl substrates.

Example 11

Measuring ADAMTS13 Antigen in Plasma Using ELISA

Figure 13:
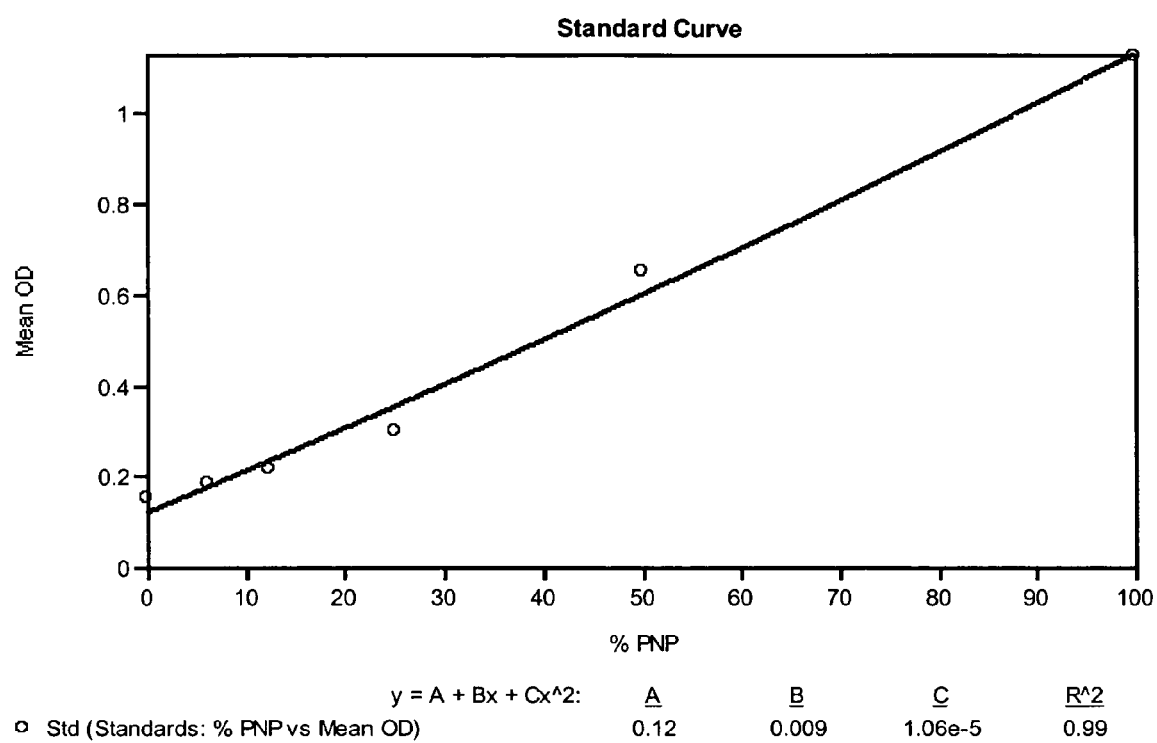
FIG. 13 shows a standard curve depicting concentration dependent increase in optical density using the ADAMTS13 ELISA and different amounts of normal plasma.

An ELISA for measuring ADAMTS13 protein in biological fluids was developed. Immulon 4 96-well microtiter plates (Dynex) were coated with goat anti-ADAMTS13 antibody (2 µg/ml) in 100 µl of 50 mM MOPS buffer pH 6.0. Plates were washed and blocked with Superblock (Pierce, Ind.). A PNP sample was serially diluted 1:2 in buffer and 100 µl was added to microtiter wells. After incubation for 1 hour at 37° C., the plate was washed and 0.5 µg/ml immunoglobulin purified from plasma obtained from a patient with acquired TTP was added to the microtiter wells. After incubation at 37° C. for 1 hour, the plate was washed and donkey anti-human Ig-HRP labeled antibody (Jackson Laboratories, Me.) (1:1000) was added to the wells. After incubation for 1 hour at 37° C., the plate was washed and 100 µl TMB substrate (Moss Inc, Md.) was added to each well. The plate was incubated at room temperature for 5 minutes and the reaction was stopped by adding 50 µl of 0.45 M sulfuric acid. The absorbance at 450 nm was measured. FIG. 13 shows the increase in absorbance was linearly proportional to the amount of ADAMTS13-containing plasma added.

Figure 14:
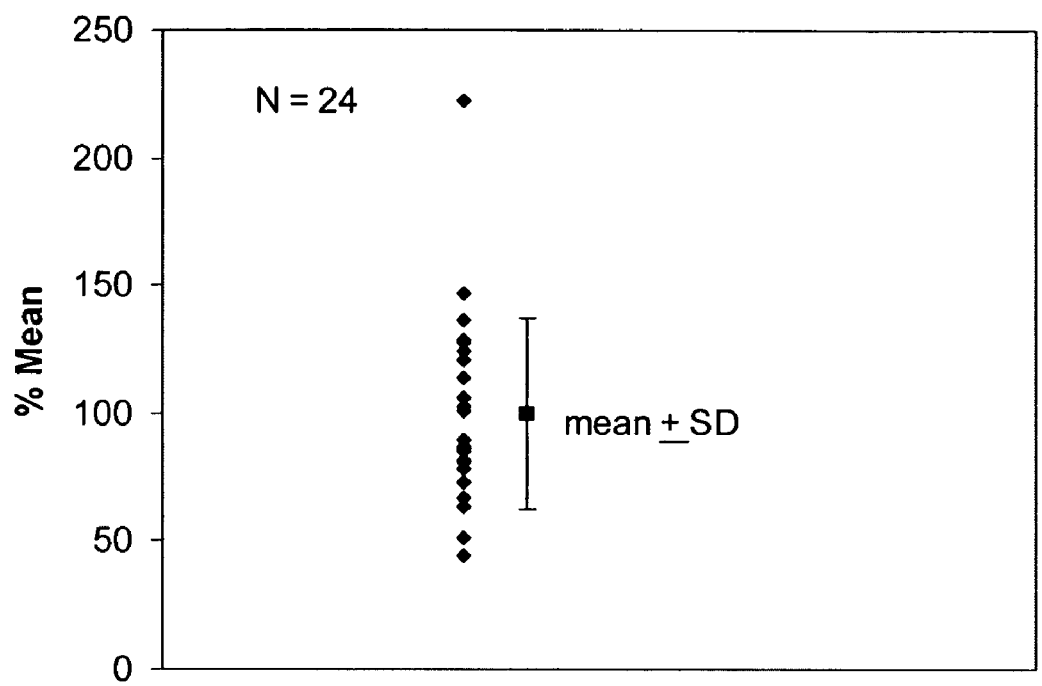
FIG. 14 shows the determination of ADAMTS13 levels, relative to pooled normal plasma (PNP), in twenty-four individual plasma samples from normal subjects using the ELISA method.

In another experiment, the amount of ADAMTS13 protein in 24 normal plasma samples was determined using the ELISA method. The results are shown in FIG. 14. Using PNP as 100%, the amount of ADAMTS13 in 24 individual normal plasma samples was distributed around the PNP value. This ELISA method can be used to determine the amount of ADAMTS13 in plasma and other biological fluids.

Example 12

Inhibition of Recombinant ADAMTS13 Activity by Goat anti-ADAMTS13 Antibody

Figure 15:
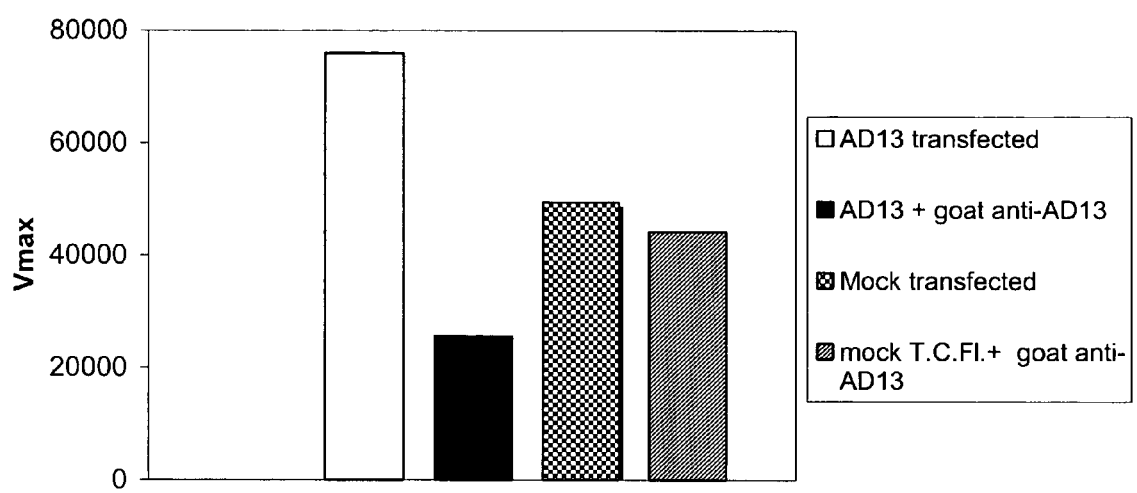
FIG. 15 shows inhibition of recombinant ADAMTS13 activity by goat anti-ADAMTS13 antibody.

Tissue culture fluid (5 µl) from HEK 293 cells transfected with a vector coding for recombinant ADAMTS13 or tissue culture fluid (5 µl) from mock transfected HEK 293 cells was added to 5 µl of goat anti-ADAMTS13 antibody (Santa Cruz Biochemicals, Santa Cruz, CA) and 0.8 mM Suc-LLVY-AMG (SEQ ID NO: 2) fluorescent substrate in 50 mM Tris-HCl pH 8.0 buffer (85 µl). The fluorescence (Vmax) was followed in a spectrofluorometric plate reader at Ex 360 nm/Em 440 nm (FIG. 15).

ADAMTS13 culture fluid had more fluorescence activity than the mock transfected culture fluid. The goat anti-ADAMTS13 antibody inhibited the fluorescence from them ADAMTS 13 fluid but not from the tissue culture fluid from mock transfected cells. These results show that the fluorescence activity from the fluid from mock transfected cells is not due to ADAMTS13.

Example 13

Inhibition of Recombinant ADAMTS13 Activity by Acquired TTP Plasma

Figure 16:
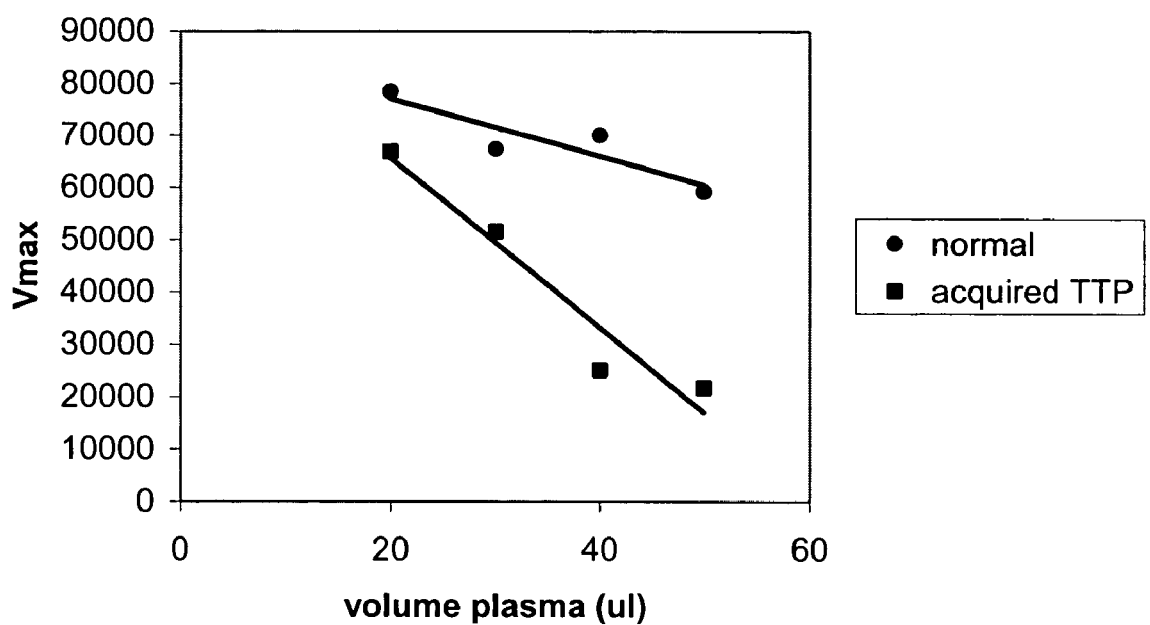
FIG. 16 shows recombinant ADAMTS13 activity in the presence of varying amounts of normal plasma or plasma from subjects with acquired TTP, which contains an inhibitor of the enzyme.

Plasma from patients with acquired TTP ("acquired TTP plasma") contains an inhibitory antibody against ADAMTS 13. FIG. 16 shows that the addition of TTP plasma to tissue culture supernatant containing recADAMTS 13 inhibited the generation of a fluorescence signal when Suc-LLVY-AMC (SEQ ID NO: 2) was used as a substrate. The amount of inhibition of fluorescence signal was dependent on the amount of TTP plasma added. Plasma from healthy subjects ("normal plasma") did not significantly inhibit ADAMTS13 activity, as compared to acquired TTP plasma, demonstrating the ADAMTS 13 activity was specifically inhibited by the acquired TTP plasma. These studies also show that antibodies present in acquired TTP plasmas block hydrolysis of the fluorescent Suc-LLVY-AMC (SEQ ID NO: 2) substrate by recombinant ADAMTS 13.

Example 14

Figure 17:
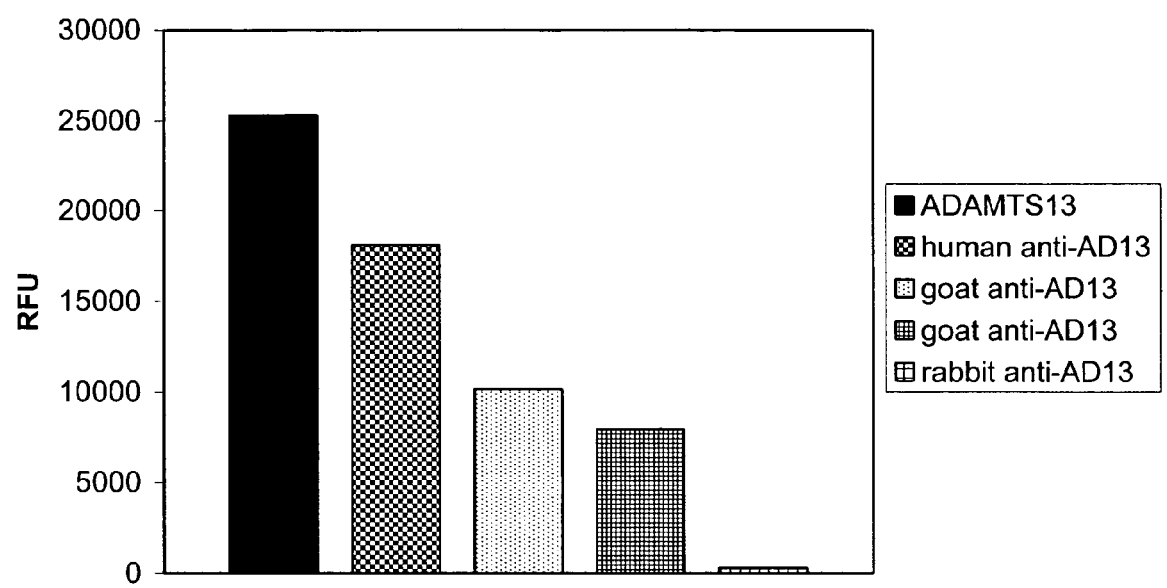
FIG. 17 shows inhibition of ADAMTS13 activity on isolated platelets by anti-ADAMTS13 antibodies from different species.

Inhibition of ADAMTS13 Activity on Isolated Platelets by Anti-ADAMTS13 Antibodies One ml of PRP was centrifuged at 10,000 rpm and the platelets in the pellet were washed with 50 mM Tris-HCl pH 8.0 buffer. The platelets were suspended in 200 µl of assay buffer. Isolated platelets (20 µl) were added to 70 µl of various anti-ADAMTS13 antibodies and incubated at room temperature for 15 minutes. The G1 and G2 goat antibodies (Santa Cruz Biochemicals, Santa Cruz, Calif.) were used at 200 µg/ml; the rabbit antibody against the C-terminal fragment of ADAMTS13 (from Dr. Ginsburg) was used at 5.5 mg/ml. Purified immunoglobulin (Ig) from acquired TTP plasma was used at a concentration of 4 mg/ml. Ninety µl of 10 mM Tris-HCl pH 8.0 buffer and 10 µl of 8 mM LVY-AMC were added and the fluorescence was measured over time as above. All four anti-ADAMTS13 specific antibodies inhibited the activity of normal platelets (FIG. 17). These findings indicate that the activity in platelets was due to ADAMTS13 cleaving the LVY-AMC substrate.

Example 15

Figure 18:
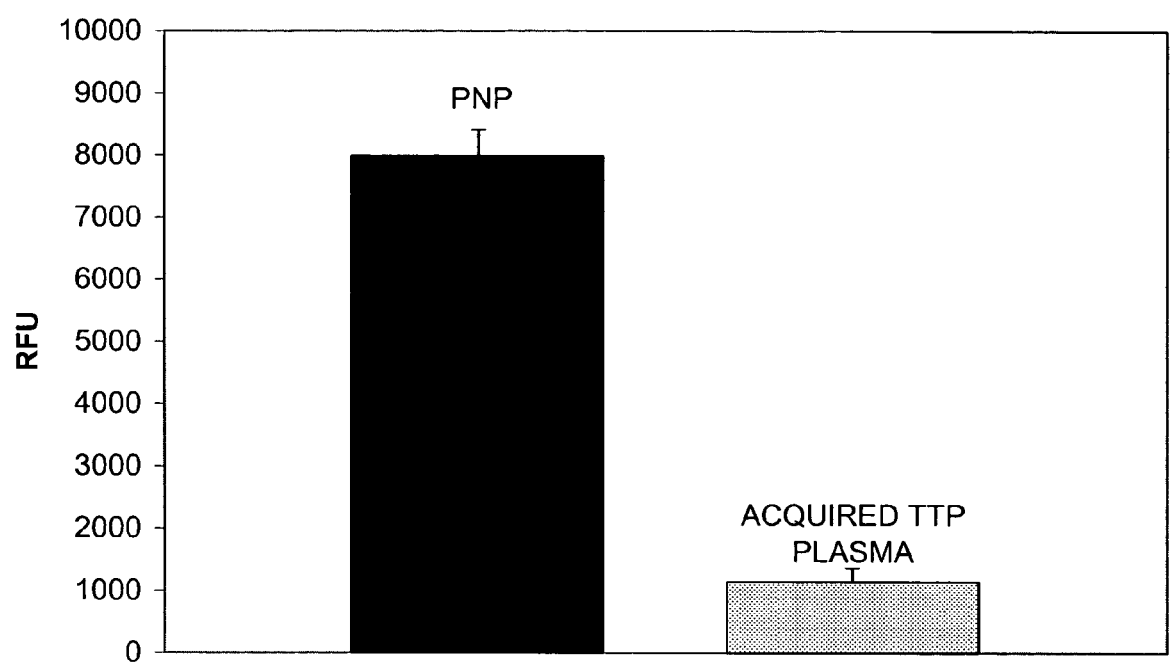
FIG. 18 shows the results of an experiment measuring anti-ADAMTS13 autoantibodies in plasma by preincubating sample plasma with isolated normal platelets.

A Method for Measuring Anti-ADAMTS13 Antibodies in Plasma Using Isolated Platelets Detection of anti-ADAMTS13 autoantibodies was performed using isolated platelets as a source of ADAMTS13. Isolated platelets (prepared from 200 µL of normal PRP) were incubated with 200 µL pooled normal plasma (PNP) or acquired TTP plasma. The mixtures were incubated at 37° C. for 30 minutes. Fifty µl were removed from each reaction mixture and added to 130 µl of 50 mM Tris-HCl pH 8.0 buffer and 20 µL of 8 mM LVY-AMC substrate. The reaction mixtures were incubated for 30 minutes at 37° C. for one hour and fluorescence was monitored in a spectrofluorometric plate reader (Ex 360 nm/Em 440 nm). The platelets incubated with normal plasma had high fluorescence signal (indicating high ADAMTS13 activity), whereas the platelets incubated with acquired TTP plasma had low fluorescence signal (indicating low ADAMTS13 activity) (FIG. 18). These results show that anti-ADAMTS13 autoantibodies were present in the acquired TTP plasma, but not in the normal plasma, and that autoantibodies in plasma from a patient with acquired TTP can be detected using this method. Other fluorescent ADAMTS13 substrates can be substituted for LVY-AMC. This method can be used to distinguish between congenital TTP and acquired TTP.

Figure 19:
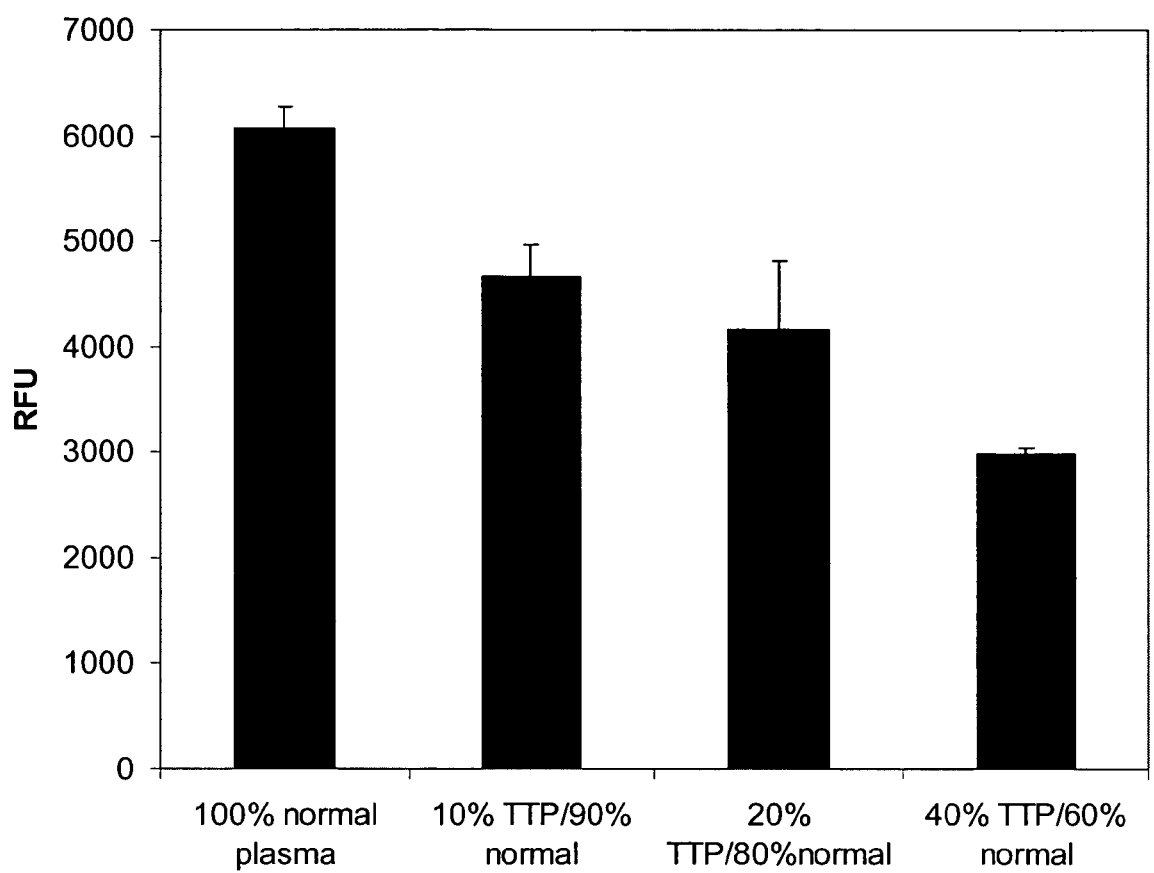
FIG. 19 shows concentration dependent inhibition of platelet ADAMTS13 activity by human ADAMTS13 antibodies in plasma from subjects with acquired TTP.

FIG. 19 shows that the level of inhibition of ADAMTS13 activity on platelets is dependent on the amount of anti-ADAMTS13 autoantibodies used in the assay, and thus the anti-ADAMTS13 activity. Plasma from an acquired TTP patient was diluted to different amounts (10%, 20% and 40%) in normal plasma and incubated with isolated platelets in a total volume of 90 µl for 15 minutes. Ten µl of 8 mM LVY-AMC substrate was added and the fluorescence was determined after incubation at 37° C. for 1 hour. The inhibition of ADAMTS13 activity by TTP plasma was dependent upon the amount of TTP plasma used in the assay.

Figure 20:
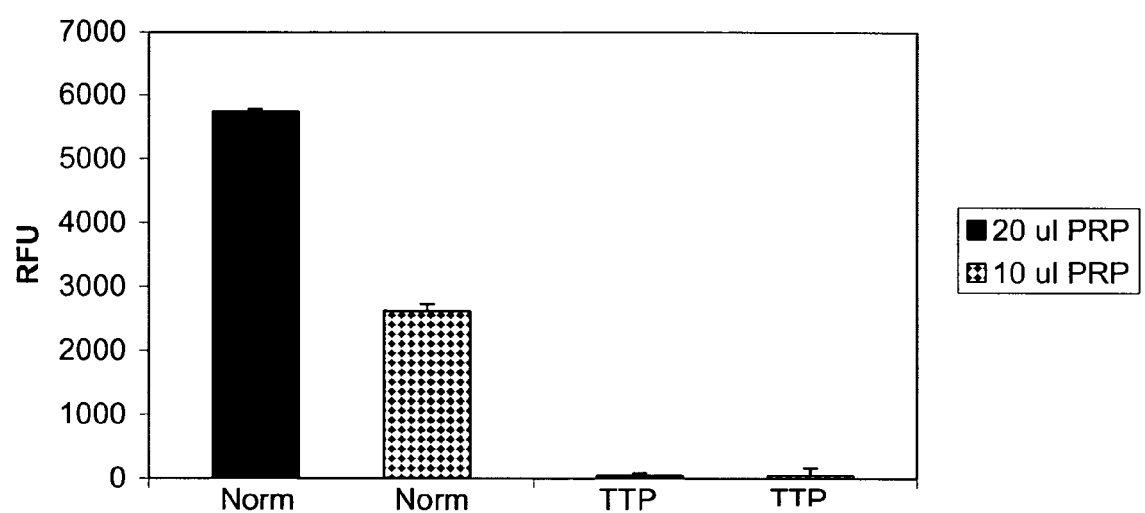
FIG. 20 shows the effect of using different amounts of platelets in the fluorescence assay of the invention. ADAMTS13 activity was measured in PRP from normal subjects and subjects with acquired TTP.

The amount of fluorescence generated over time in the assay is dependent upon the amount of platelets used in the assay. As shown in FIG. 20, a higher fluorescent signal was generated in the control (normal plasma without anti-ADAMTS13 antibodies) using more platelets. The addition of acquired TTP plasma, containing ADAMTS13 antibodies, almost completely inhibited ADAMTS13 activity, regardless of the amount of platelets in the assay.

All documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

---

We claim:

1. A method for measuring the presence of platelet ADAMTS13 comprising:
   a) incubating a sample comprising ADAMTS13 with a substrate, wherein the sample is selected from the group consisting of platelet rich plasma (PRP), pooled normal plasma (PNP) and washed platelets, wherein the substrate comprises a peptide moiety and a chromogenic or fluorogenic moiety, wherein the peptide moiety comprises X-Val-Tyr, X-Leu-Tyr or X-Ile-Tyr, wherein X is any amino acid, and wherein the chromogenic moiety is not para-nitroanaline (pNA); and
   b) measuring optical density or fluorescence of the sample;
   thereby measuring the presence of platelet ADAMTS13.

2. The method of claim 1, wherein X is Leu.

3. The method of claim 1, wherein the peptide moiety is Leu-Val-Tyr.

4. The method of claim 1, wherein the peptide moiety is Leu-Leu-Val-Tyr (SEQ ID NO:2).

5. The method of claim 1, wherein the peptide moiety is Suc-Leu-Leu-Val-Tyr (Suc-SEQ ID NO:2).

6. The method of claim 1, wherein the chromogenic moiety is selected from the group consisting of s-benzyl, 5-amino-2-nitrobenzoic acid and 6-amino-1-naphthalene-sulfonamides.

7. The method of claim 1, wherein the fluorogenic moiety is selected from the group consisting of coumarins, fluoresceins, rhodamines, resorufins and dimethylacridinones.

8. The method of claim 7, wherein the fluorogenic moiety is a coumarin.

9. The method of claim 8, wherein the coumarin is 7-amino-4-methylcoumarin (AMC).

10. A method for measuring the presence of platelet ADAMTS13 comprising:
    a) incubating a sample comprising ADAMTS13 with a substrate, wherein the sample is selected from the group consisting of PRP, PNP and washed platelets, wherein the substrate comprises X-peptide moiety-Z, wherein the peptide moiety comprises Val-Tyr-Met, Leu-Tyr-Met or Ile-Tyr-Met, wherein X is a donor moiety and Z is an acceptor moiety, and wherein the donor and acceptor moieties mediate fluorescence resonance energy transfer; and
    b) measuring fluorescence of the sample;
    thereby measuring the presence of platelet ADAMTS13.

11. The method of claim 10, wherein the peptide moiety is Asn-Leu-Val-Tyr-Met-Val-Thr-Gly-Asp (SEQ ID NO:3).

12. The method of claim 10, wherein the donor moiety is EDANS.

13. The method of claim 12, wherein the acceptor moiety is DABCYL.

14. The method of claim 10, wherein the substrate is $NH_2$-Arg-Lys-(DABCYL)-Asn-Leu-Val-Tyr-Met-Val-Thr-Gly-Asp-(EDANS)-Arg-COOH-($NH_2$-Arg-Lys-(DABCYL)-SEQ ID NO:3-(EDANS)-Arg-COOH)—.

15. A method for identifying an inhibitor of platelet ADAMTS13 comprising:
    a) incubating a sample comprising platelet ADAMTS13 with a candidate inhibitor of ADAMTS13, wherein the sample is selected from the group consisting of PRP, PNP and washed platelets; and
    b) incubating the sample with a substrate comprising a peptide moiety and a chromogenic or fluorogenic moiety, wherein the peptide moiety comprises X-Val-Tyr, X-Leu-Tyr or X-Ile-Tyr, wherein X is any amino acid and wherein the chromogenic moiety is not pNA; and
    c) measuring the optical density or fluorescence of the sample;
    wherein the inhibitor is identified by reduced optical density or fluorescence of the sample compared with optical density or fluorescence of a control sample comprising platelet ADAMTS13, wherein the control sample is selected from the group consisting of PRP, PNP and washed platelets, and wherein the control sample was not incubated with the candidate inhibitor.

16. The method of claim 15, wherein X is Leu.

17. The method of claim 15, wherein the peptide moiety is Leu-Val-Tyr.

18. The method of claim 15, wherein the peptide moiety is Leu-Leu-Val-Tyr (SEQ ID NO:2).

19. The method of claim 15, wherein the peptide moiety is Suc-Leu-Leu-Val-Tyr (Suc-SEQ ID NO:2).

20. The method of claim 15, wherein the chromogenic moiety is selected from the group consisting of s-benzyl, 5-amino-2-nitrobenzoic acid and 6-amino-1-naphthalene-sulfonamides.

21. The method of claim 15, wherein the fluorogenic moiety is selected from the group consisting of coumarins, fluoresceins, rhodamines, resorufins and dimethylacridinones.

22. The method of claim 21, wherein the fluorogenic moiety is a coumarin.

23. The method of claim 22, wherein the coumarin is 7-amino-4-methylcoumarin (AMC).

24. The method of claim 15, wherein the candidate inhibitor is from a chemical compound library, a phage display library, a natural chemical library or a combinatorial chemistry library.

25. The method of claim 15, wherein the inhibitor is an antibody.

26. A method for identifying an inhibitor of platelet ADAMTS13 comprising:
  a) incubating a sample comprising platelet ADAMTS13 with a candidate inhibitor of ADAMTS13, wherein the sample is selected from the group consisting of PRP, PNP and washed platelets; and
  b) incubating the sample with a substrate comprising a peptide moiety and a chromogenic or fluorogenic moiety, wherein the peptide moiety comprises X-Val-Tyr, X-Leu-Tyr or X-Ile-Tyr, wherein X is any amino acid and wherein the chromogenic moiety is not pNA; and
  c) measuring the optical density or fluorescence of the sample;
  wherein the inhibitor is identified by reduced optical density or fluorescence of the sample compared with optical density or fluorescence of a control sample comprising platelet ADAMTS13, wherein the control sample is selected from the group consisting of PRP, PNP and washed platelets, and wherein the control sample was not incubated with the candidate inhibitor.

27. The method of claim 26, wherein the peptide moiety is Asn-Leu-Val-Tyr-Met-Val-Thr-Gly-Asp (SEQ ID NO:3).

28. The method of claim 26, wherein the donor moiety is EDANS.

29. The method of claim 28, wherein the acceptor moiety is DABCYL.

30. The method of claim 26, wherein the substrate is NH$_2$-Arg-Lys-(DABCYL)-Asn-Leu-Val-Tyr-Met-Val-Thr-Gly-Asp-(EDANS)-Arg-COOH (NH$_2$-Arg-Lys-(DABCYL)-SEQ ID NO:3-(EDANS)-Arg-COOH)—.

31. The method of claim 26, wherein the candidate inhibitor is from a chemical compound library, a phage display library, a natural chemical library or a combinatorial chemistry library.

32. The method of claim 26, wherein the inhibitor is an antibody.

33. A method for diagnosing TTP in a subject comprising:
  a) measuring the amount of platelet ADAMTS13 in a test sample from the subject according to the method of claim 1, wherein the test sample is selected from the group consisting of PRP and washed platelets; and
  b) comparing the amount of platelet ADAMTS13 in the test sample to the amount of platelet ADAMTS13 in a control sample having a normal amount of platelet ADAMTS13 wherein the control sample is selected from the group consisting of PRP, PNP and washed platelets;
  wherein TTP is diagnosed by reduced amount of platelet ADAMTS13 in the test sample compared with the control sample.

34. The method of claim 33, wherein X is Leu.

35. The method of claim 33, wherein the peptide moiety is Leu-Val-Tyr.

36. The method of claim 33, wherein the peptide moiety is Leu-Leu-Val-Tyr (SEQ ID NO:2).

37. The method of claim 33, wherein the peptide moiety is Suc-Leu-Leu-Val-Tyr (Suc-SEQ ID NO:2).

38. The method of claim 33, wherein the chromogenic moiety is selected from the group consisting of s-benzyl, 5-amino-2-nitrobenzoic acid and 6-amino-1-naphthalene-sulfonamides.

39. The method of claim 33, wherein the fluorogenic moiety is selected from the group consisting of coumarins, fluoresceins, rhodamines, resorufins and dimethylacridinones.

40. The method of claim 39, wherein the fluorogenic moiety is a coumarin.

41. The method of claim 40, wherein the coumarin is 7-amino-4-methylcoumarin (AMC).

42. The method of claim 33, wherein the TTP is congenital.

43. The method of claim 33, wherein the TTP is acquired.

44. A method for diagnosing TTP in a subject comprising:
  a) measuring the amount of platelet ADAMTS13 in a test sample from the subject according to the method of claim 10, wherein the test sample is selected from the group consisting of PRP and washed platelets; and
  b) comparing the amount of platelet ADAMTS13 in the test sample to the amount of platelet ADAMTS13 in a control sample having a normal amount of platelet ADAMTS13, wherein the control sample is selected from the group consisting of PRP, PNP and washed platelets;
  wherein TTP is diagnosed by reduced amount of platelet ADAMTS13 activity in the test sample compared with the control sample.

45. The method of claim 44, wherein the peptide moiety is Asn-Leu-Val-Tyr-Met-Val-Thr-Gly-Asp (SEQ ID NO:3).

46. The method of claim 44, wherein the donor moiety is EDANS.

47. The method of claim 46, wherein the acceptor moiety is DABCYL.

48. The method of claim 44, wherein the substrate is NH$_2$-Arg-Lys-(DABCYL)-Asn-Leu-Val-Tyr-Met-Val-Thr-Gly-Asp-(EDANS)-Arg-COOH (NH$_2$-Arg-Lys-(DABCYL)-SEQ ID NO:3-(EDANS)-Arg-COOH)—.

49. The method of claim 44, wherein the TTP is congenital.

50. The method of claim 44, wherein the TTP is acquired.

51. A method for diagnosing acquired TTP in a subject comprising:

a) incubating a sample comprising platelet ADAMTS13 with plasma from the subject, wherein the sample is selected from the group consisting of PRP, PNP and washed platelets; and b) measuring the amount of platelet ADAMTS13 in the sample according to the method of claim 1;

wherein acquired TTP is diagnosed by reduced amount of platelet ADAMTS13 activity in the sample compared with the amount of platelet ADAMTS13 in a control sample having a normal amount of platelet ADAMTS13.

52. The method of claim 51, wherein X is Leu.

53. The method of claim 51, wherein the peptide moiety is Leu-Val-Tyr.

54. The method of claim 51, wherein the peptide moiety is Leu-Leu-Val-Tyr (SEQ ID NO:2).

55. The method of claim 51, wherein the peptide moiety is Suc-Leu-Leu-Val-Tyr (Suc-SEQ ID NO:2).

56. The method of claim 51, wherein the chromogenic moiety is selected from the group consisting of s-benzyl, 5-amino-2-nitrobenzoic acid and 6-amino-1-naphthalene-sulfonamides.

57. The method of claim 51, wherein the fluorogenic moiety is selected from the group consisting of coumarins, fluoresceins, rhodamines, resorufins and dimethylacridinones.

58. The method of claim 57, wherein the fluorogenic moiety is a coumarin.

59. The method of claim 58, wherein the coumarin is 7-amino-4-methylcoumarin (AMC).

60. A method for diagnosing acquired TTP in a subject comprising:

a) incubating a sample comprising platelet ADAMTS13 with plasma from the subject, wherein the sample is selected from the group consisting of PRP, PNP and washed platelets; and b) measuring the amount of platelet ADAMTS13 in the sample according to the method of claim 12;

wherein acquired TTP is diagnosed by reduced amount of platelet ADAMTS13 in the sample compared with the amount of platelet ADAMTS13 in a control sample having a normal amount of platelet ADAMTS 13.

61. The method of claim 60, wherein the peptide moiety is Asn-Leu-Val-Tyr-Met-Val-Thr-Gly-Asp (SEQ ID NO:3).

62. The method of claim 60, wherein the donor moiety is EDANS.

63. The method of claim 62, wherein the acceptor moiety is DABCYL.

64. The method of claim 60, wherein the substrate is $NH_2$-Arg-Lys-(DABCYL)-Asn-Leu-Val-Tyr-Met-Val-Thr-Gly-Asp-(EDANS)-Arg-COOH ($NH_2$-Arg-Lys-(DABCYL)-SEQ ID NO:3(EDANS)-Arg-COOH)—.

* * * * *

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(DABCYL)
<220> FEATURE:
<221> NAME/KEY: MOD_RES
<222> LOCATION: (11)
<223> OTHER INFORMATION: Asp(EDANS)
```

-continued

```
<400> SEQUENCE: 1

Arg Lys Asn Leu Val Tyr Met Val Thr Gly Asp Arg
 1               5                  10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Leu Val Tyr
 1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Leu Val Tyr Met Val Thr Gly Asp
 1               5
```